US007932264B2

(12) United States Patent
Wang et al.

(10) Patent No.: US 7,932,264 B2
(45) Date of Patent: Apr. 26, 2011

(54) SINOMENINE DERIVATIVES AND PREPARATION AND USES THEREOF

(75) Inventors: Jie Wang, Englewood Cliffs, NJ (US); Yi Pan, Jiansu (CN)

(73) Assignee: Naturemed Group Corporation, Englewood Cliffs, NJ (US)

( * ) Notice: Subject to any disclaimer, the term of this patent is extended or adjusted under 35 U.S.C. 154(b) by 337 days.

(21) Appl. No.: 12/096,543

(22) PCT Filed: Dec. 15, 2006

(86) PCT No.: PCT/US2006/048086
§ 371 (c)(1),
(2), (4) Date: Jun. 6, 2008

(87) PCT Pub. No.: WO2007/070703
PCT Pub. Date: Jun. 21, 2007

(65) Prior Publication Data
US 2008/0318966 A1   Dec. 25, 2008

(30) Foreign Application Priority Data

| Dec. 15, 2005 | (CN) | 2005 1 0123089 |
| Dec. 15, 2005 | (CN) | 2005 1 0123090 |
| Mar. 15, 2006 | (CN) | 2006 1 0038862 |

(51) Int. Cl.
*C07D 221/28* (2006.01)
*A61K 31/485* (2006.01)

(52) U.S. Cl. .......................... 514/289; 546/74
(58) Field of Classification Search .................. 546/74; 514/289
See application file for complete search history.

(56) References Cited

U.S. PATENT DOCUMENTS

| 6,372,756 B1 | 4/2002 | Christians et al. |
| 7,144,710 B2 | 12/2006 | Guyre et al. |
| 2003/0215885 A1 | 11/2003 | Guyre et al. |

FOREIGN PATENT DOCUMENTS

| CN | 1153171 | 7/1997 |
| CN | 200680047418.1 | 6/2008 |
| CN | 101578101 | 11/2009 |
| EP | 06847694.4 | 6/2008 |
| EP | 1959956 | 8/2008 |
| JP | 2008-5458 | 6/2008 |
| JP | 2009519960 | 5/2009 |
| WO | WO 2004/048340 A1 | 6/2004 |
| WO | WO 2007/070703 A2 | 6/2007 |

OTHER PUBLICATIONS

Liu, Liang; "Inhibition of lymphocyte proliferation by the anti-arthritic drug sinomenine." International Journal of Immunopharmacology, 16(8), 685-91 1994 (abstract only).*
Fang, Yongfei; "Effects and mechanism of sinomenine on signal transduction of synovial cell nuclear factor-κB in rats with adjuvant arthritis." Zhongguo Linchuang Kangfu, 9(7), 204-205 2005 (abstract only).*
Dorwald F. A. Side Reactions in Organic Synthesis, 2005, Wiley: VCH, Weinheim p. IX of Preface.*
Candinas et. al. "Immunomodulatory Effects of the Alkaloid Sinomenine in the High Responder ACI-to-Lewis Cardiac Allograft Model 1" Transplantation Dec. 27, 1996 vol. 62(12), pp. 1855-1860.*
PCT International Search Report issued Oct. 2, 2007 for NatureMed Group Corporation et al., International App'l No. PCT/US2006/048086, filed Dec. 15, 2006.
PCT Written Opinion of the International Searching Authority issued Oct. 2, 2007 for NatureMed Group Corporation et al., International App'l No. PCT/US2006/048086, filed Dec. 15, 2006.
Ju et al., 2010, "Protective Effect of Sinomenine on Cartilage Degradation and Chondrocytes Apoptosis", Yakugaku Zasshi, vol. 130(8): 1053-1060.
Ou et al., 2010, "Sinomenine Reduces Invasion and Migration Ability in Fibrolast-like Synoviocytes Cells Co-cultured with activated human monocytic THP-1 cells by Inhibiting the Expression of MMP-2, MMP-9, CD147", Rheumatol Int., Epub ahead of print.
Li et al., 2010, "Sinomenine, theophylline, cysteine, and levamisole: Comparisons of their kinetic effects on mineral formation induced by matrix vesicles", J. Inorg Biochem, vol. 104(4): 446-454.
Li et al., 2010, "Development of Patch and Spray Formulations for Enhancing Topical Delivery of Sinomenine Hydrochloride", J. Pharm. Sci. vol. 99(4): 1790-1799.
Ou et al., 2009, "Sinomenine Reduces Invasion and Migration Ability in Fibrolast-like Synoviocytes Cells Co-cultured with activated human monocytic THP-1 cells by Inhibiting the Expression of MMP-2, MMP-9, CD147", Acta Pharmacol. Sin., vol. 30(4):435-441.
Zhou et al., 2008, "Sinomenine Ameliorates Arthritis via MMPs, TIMPs, and Cytokines in Rats", Biochemical and Biophysical Research Communications, vol. 376(2):352-357.
Xu et al., 2008, "Sinomenine versus NSAIDs for the Treatment of Rheumatoid Arthritis: a Systematic Review and Meta-Analysis", Planta Med., vol. 74(12):1423-1429.
Deng et al., 2008, "pH-dependent, Steroselective Dimerization of Sinomenine", Org Left., vol. 10 (17):3879-3882.
Deng et al., 2008, "Biocatalyzed Cross-Coupling of Sinomenine and Guaiacol by Antrodiella", Org Lett., vol. 10 (6):1119-1122.
Wang et al., 2007, "Voltammetric Determination of Sinomenine in Biological Gluid Using a Glassy Carbon Electrode Modified by a Composite Film of Polycysteic Acid and Carbon Nanotudes", Comb Chem. High Throughput Screen, vol. 10(7):595-603.
Wang et al., 2007, "Sinomenine Inhibits Activation of rat retinal microglia induced by advanced glycation end products", Int. Immunopharmacol., vol. 7(12).1552-1558.
Kok et al., 2005, "The Anti-angiogenic Effect of Sinomenine", Angiogenesis, vol. 8(1):3-12.

(Continued)

*Primary Examiner* — Rita J Desai
*Assistant Examiner* — David K O'Dell
(74) *Attorney, Agent, or Firm* — Law Offices of Albert Wai-Kit Chan, PLLC

(57) ABSTRACT

The present invention relates to the preparation and pharmacological use of sinomenine derivatives of formula I. The approach disclosed herein is the modification of D ring by-substituting for R. Additional substitutions in the other rings are also provided herein. Several of the sinomenine derivatives have significantly greater anti-inflammation activity when compared with the parent compound.

8 Claims, 11 Drawing Sheets

OTHER PUBLICATIONS

Liu et al., 2005, "Influence of Co-Administered Sinomenine on Pharmacokinetic Fate of Paeoniflorin in Unrestrained Conscious Rats", J. Ethnopharmacol., vol. 99(1):61-67.

Zhang et al., 2009, "Research Advances of Mechanism of Sinomenine in Treating Rheumatoid Arthritis", Journal of Chinese Integrative Medicine, vol. 7(8): 775-778. (w/English abstract).

Yu et al., 2009, "Effect of Sinomenine on the Expression of Chemokines and Chemokine Receptors in Dendritic Cells from Patients with Rheumatoid Arthritis", Nan Fang Yi Ke Da Xue Xue Bao, vol. 29(4): 635-637. (abstract only).

Liu et al., 2005, "Immunopharmacological Action of Sinomenine, and Alkaloid Isolated from Sinomenium Acutum, and its Mechanism of action in Treating Rheumatoid Arthritis", Yao Xue Xue Bao, vol. 40(2):127-131. (abstract only).

Tu et al., 1999, "Effect of Sinomenine on IL-8, IL-6, IL-2 Produced by Peripheral Blood Mononuclear Cells", J. Tongji. Med. Univ., vol. 19(4):257-259.

Wang et al., 2002, "Study Progress in Sinomenine Acutum(Tunb.) Rehd. Et Wils", Zhong Yao Cai, vol. 25(3): 209-211. (abstract only.

Okuda, et al., 1995, A Case of Drug Eruption Cause by the Crude Drug Boi (Sinomenium stem/Sinomeni Caulk et Rhizoma), Journal of DEmatology, vol. 22 (10):795-800. (abstract only).

Yamasaki, et al., 1976, "Pharmacology of Sinomenine, an Anti-Rheumatic Alkaloid from Sinomenium Acutum", Acta. Med. Okayama., vol. 30(1):1-20.

Tang et al., Sep. 2006, "Synthesis and anti-Inflammatory activities investigation of sinomenine derivatives on ring", C. Nat Prod Res. vol. 20(11):1015-23.

Ye et al., Mar. 2004, "Synthesis and anti-inflammatory analgesic activities of sinomenine derivatives", Yao Xue Xue Bao, vol. 39(3):180-3. (w/English Abstract).

Chernoff et al., 1995, "A Randomized, Controlled Trial of IL-10 in Humans: Inhibition of Inflammatory Cytokine Production and Immune Responses", The Journal of Immunology, vol. 154:5492-5499.

Diterich et al., Jul. 2003, "Borrelia Burgdorferi-Induced Tolerance as a Model of Persistence via Immunosupression", Infection and Immunity, vol. 71(7):3979-3987.

Hamper et al., 1996, "Solid-Phase Synthesis of Proline Analogs via a Three Component 1,3-Dipolar Cycloaddition", Tetrahedron Letters, vol. 37(21):3671-3674.

Hartman et al., 1995, "The effects of anti-inflammatory and antiallergic drugs on cytokine release after Stimulation of Human Whole Blood by Lipopolysaccharide and Zymosan A", Inflamm. Res. vol. 44:269-274.

Hartung et al., 1995, "Effect of Granulocyte Colony-Stimulating Factor Treatment on Ex Vivo Blood Cytokine Response in Human Volunteers", Blood, vol. 85(9):2482-2489.

Hartung et al., 2000, "Blood Cytokine Response of Low-Dose Molgramostim (rhGM-CSF)-Treated Patients", Cytokine, vol. 12(10).1570-1574.

Hermann et al., 2003, "A Model of Human Whole Blood Lymphokine Release for in Vitro and ex Vitro Use", Journal of Immunological Methods, vol. 275: 69-79.

Hitotsuyanagi et al., 1995, "Synthesis of Antitumor Morphinane Alkaloids, Sinococuline and 6-epi-, 7-epi-, and 6-epi-7-epi-Sinococuline, from Sinomenine", Journal of Organic Chemistry, vol. 60:4549-4558.

Lagrelius et al., 2006, "Cytokine Detection by Multiplex Technology Useful for Assessing Antigen Specific Cytokine Profiles and Kinetics in Whole Blood Cultured up to Seven Days", Cytokine, vol. 33:156-165.

Zhang et al., 2004, "Characterization of (2R, 3S)-2-({[4-(2-butynyloxy)phertyl]sulfonyl})-N,3-dihydroxybutanamide, a potent and selective inhibitor of TNF-α Converting Enzyme", International Immunopharmacology, vol. 4:1845-1857.

Zhang et al., 2004, "Identification and Characterization of 4-[|4-(2-Butynyloxy)phenyl]sulfnoyl-N-hydroxy-2,2-dimethyl-(3S)-thiomorphoiinecarboxamide (TMI-1), a Novel Dual Tumor Necrosis Factor-α-Converting Enzyme/Matrix Metalloprotease inhibitor for the Treatment of Rheumatoid Arthritis", The Journal of Pharmacological and Experimental Therapeutics, vol. 309 (1):348-355.

* cited by examiner

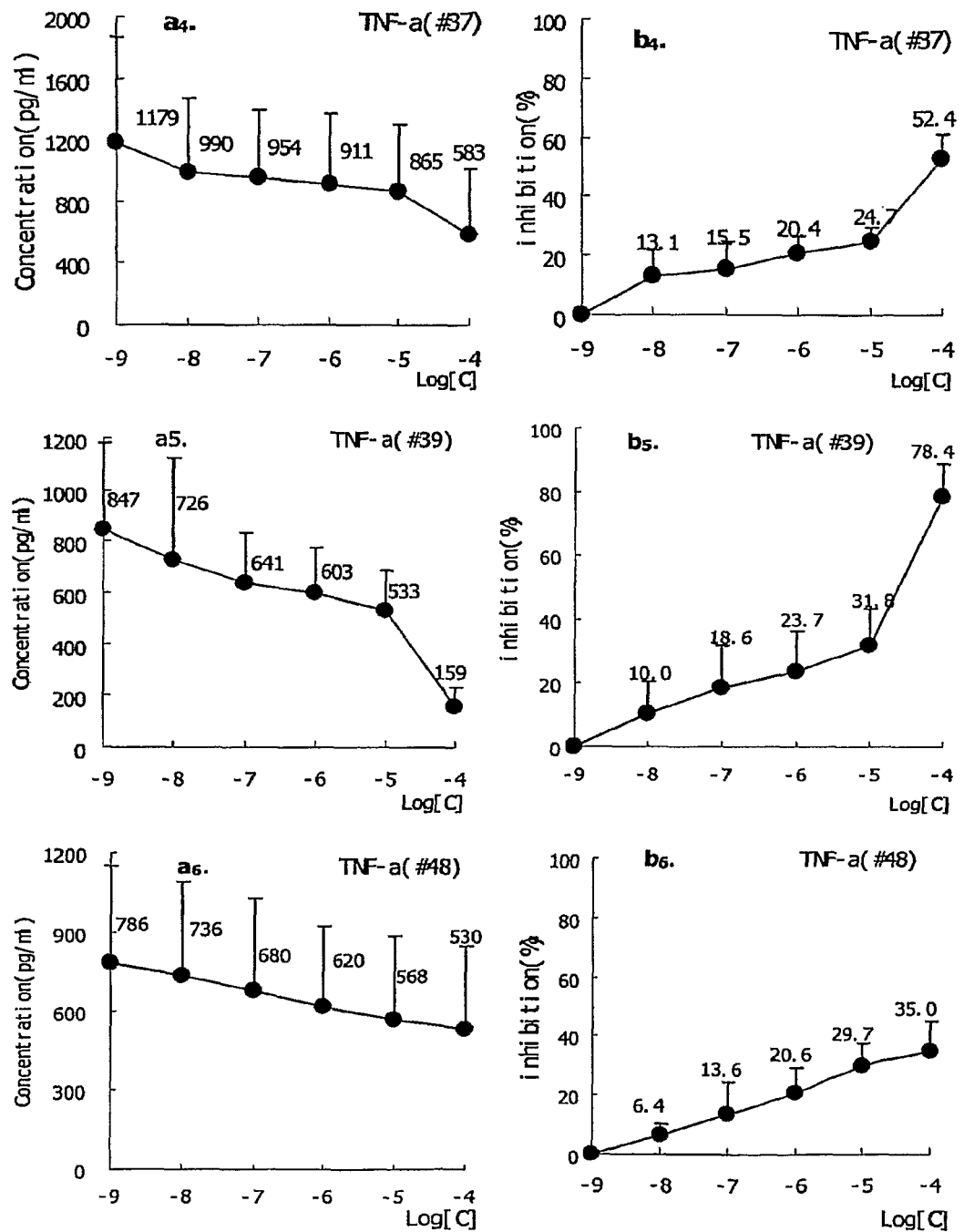
Figure 4, continued

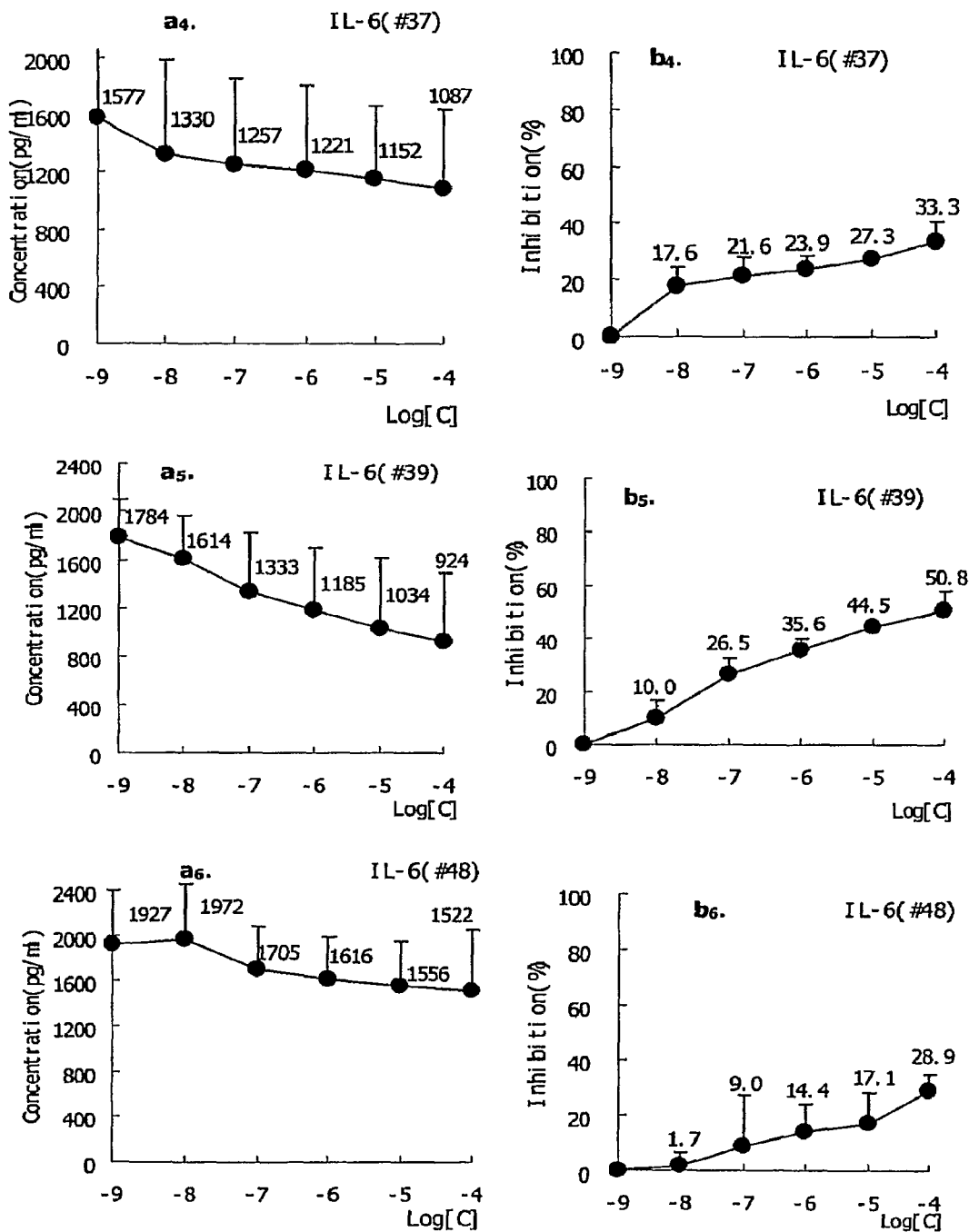
Figure 5, continued

Figure 6, continued
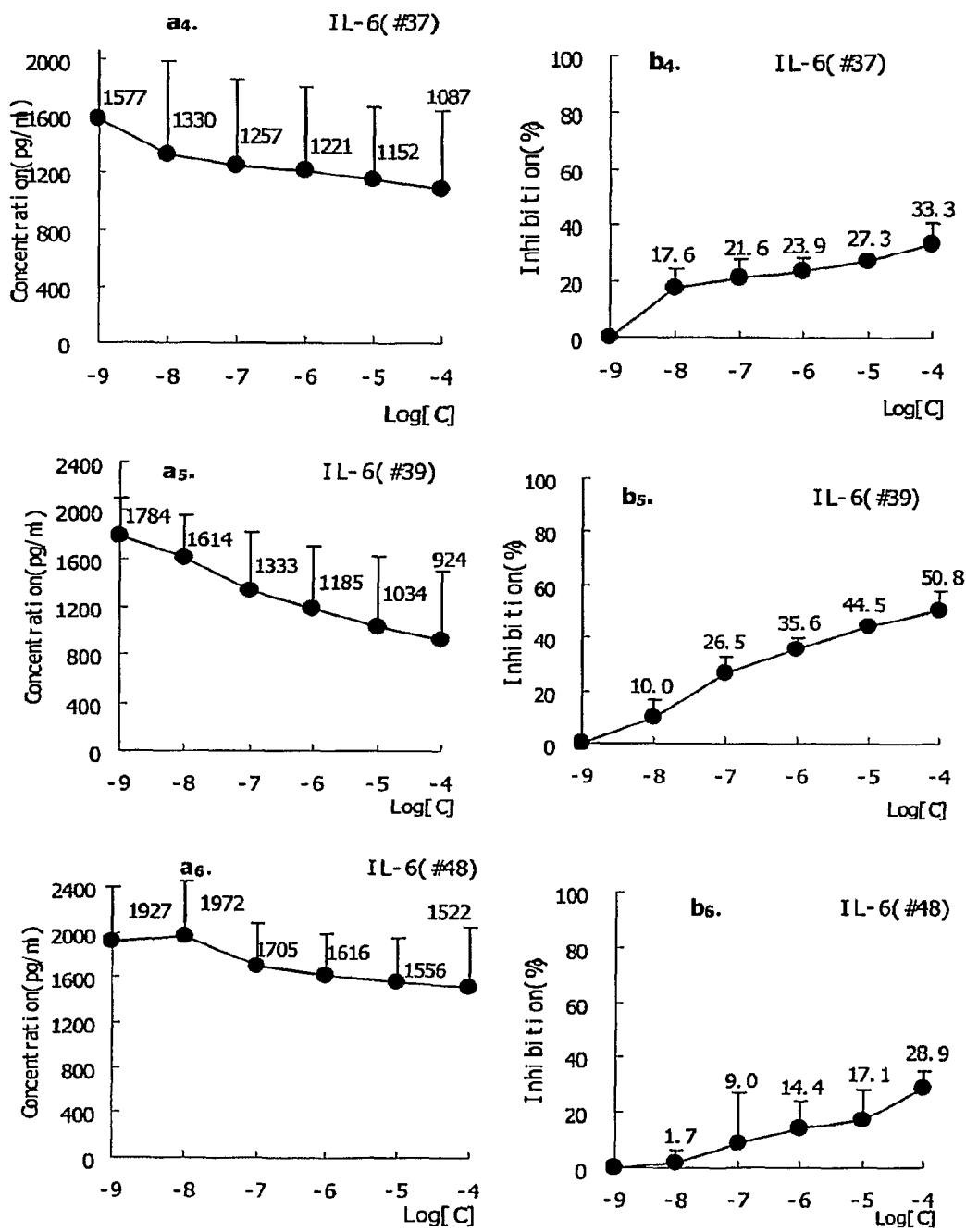

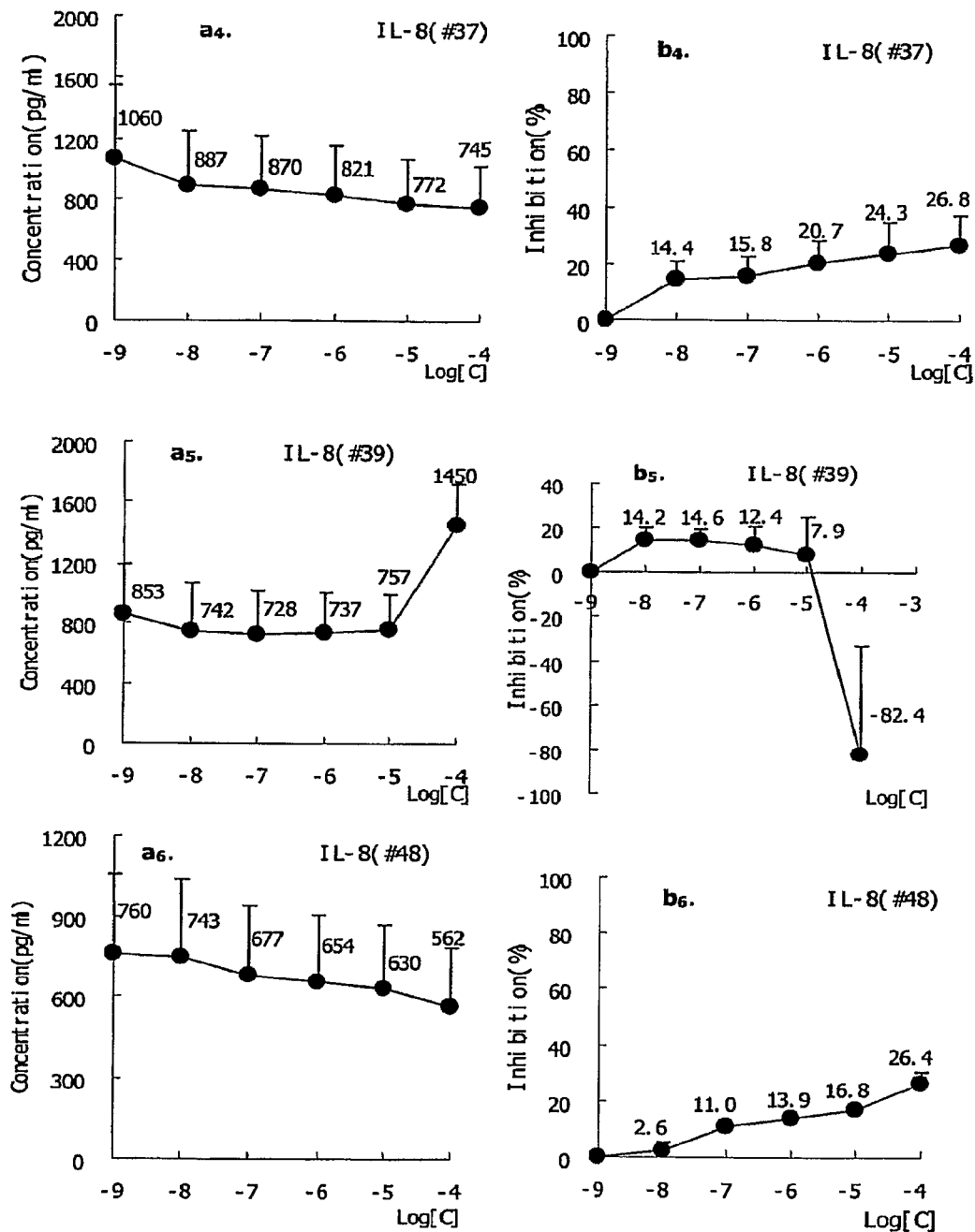
Figure 7, continued

SINOMENINE DERIVATIVES AND PREPARATION AND USES THEREOF

This application is the National Stage of Int'l App'l No. PCT/US2006/048086, filed Dec. 15, 2006, which claims priority of Chinese App'l No. 200610038862.9, filed Mar. 15, 2006, Chinese App'l No. 200510123089.1, filed Dec. 15, 2005, and Chinese App'l No. 200510123090.4, filed Dec. 15, 2005, the contents of which are incorporated in their entireties by reference into this application.

Throughout this application, various publications are referenced. The disclosures of these publications in their entireties are hereby incorporated by reference into this application to more fully describe the state of the art to which this invention pertains.

BACKGROUND OF THE INVENTION

The inflammatory response is an attempt by the body to restore and maintain tissue structure and function after injury and is an integral part of body defense. Most of the body defense elements are located in the blood and inflammation is the means by which body defense cells and defense chemicals leave the blood and enter the tissue around the injured or infected site. Although inflammation is essentially a beneficial process, excessive or prolonged inflammatory activity can result in severe pain as well as having deleterious effects on tissues.

Sinomenine, a morphine-like alkaloid derived from *sinomenum acutum*, was reported to possess anti-inflammatory, antalgic, lowering blood pressure and anti-arrhythmia activities [Wang, Naiqin, et al. *Yao Xue Xue Bao* 1992, 23(2), 81; Zhou, Jinhuang et al. <<Zhongyao Yaoli Yanjiu Yu Jinzhan>>, Chinese Science and Technology Publisher, 1993, 66; Liu, Q.; Zhou, L.-l.; Li, R. *Chinese Traditional and Herbal Drugs* 1997, 28, 247.]. Sinomenine and its hydrochloride salt have been clinically used for the treatment of rheumatoid arthritis (RA) in China. However, it suffers from a slow onset of effect and some side-effects such as tetter etc.[1] Some studies aimed at modification of sinomenine were concentrated on the reduction of the carbonyl group and hydrogenation of the double bond in the C-ring[2], while other modification was concentrated on sinomenine-metal chelate (Pang, zhigong; Wang, Baoqi. Faming Zhuanli Shenqing Gongkai Shuomingshu (1997), CN 1153171. *Chem. Abstr.* 131:356078. Kang, Jun; Xue, Chunxia; Dong, Yaling. Xibei Yaoxue Zhazhi 2000, 16 (4), 137.), however there has been little success yet achieved to enhance sinomenine activity.

Beside the above described biological activities, some new uses of sinomenine and its derivatives, such as mnemocognition-facilitating have been found in animal experimental models (Qin Guo-Wei, et al. PCT Int. Appl. (2004), WO 2004/048340, *Chem. Abstr.* 131:179808).

New derivatives of sinomenine have been conceived and implemented using a distinct approach to modifying sinomenine. Specifically, by focusing on the substitutions of the methyl group on the D-ring, derivatives were identified that enhance the biological activity of the parent sinomenine. It cannot be ruled out that the derivatives' mode of action differs from the parent compound. In sum, provided herein are numerous 17-substituted derivatives and variants of sinomenine that have improved anti-inflammation bioactivities.

DETAILED DESCRIPTION OF THE INVENTION

Figure 1A:
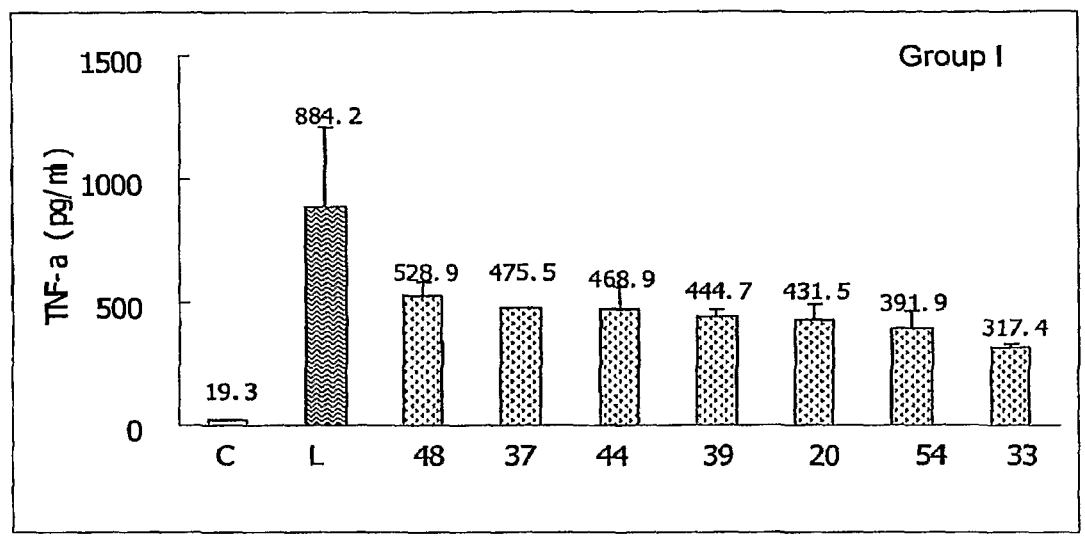
FIG. 1A. The inhibition of tumor necrosis factor alpha (TNF-α) production in human whole blood culture by seven testing compounds of Group I (concentration: $10^{-5}$ mol/L), which were each incubated in the presence of lipopolysaccharide (LPS, concentration: 10 ng/ml) for 6 h. C: Control (without LPS), L: LPS alone. Data are presented as absolute values. Mean±SD. n=2. Group I, TNF-α level <530 pg/ml: #33, #54, #20, #39, #44, #37 and #48.

The present invention relates to therapeutic compounds derived from the active agent sinomenine from *Sinomenum acutum*. Embodiments of such derivative compounds may be represented as shown below in formula (I).

The present invention also relates to embodiments of 17-substituted compounds wherein R is varied in NR thus providing embodiments of 17-substituted compounds. The naturally occurring compound, sinomenine is encompassed by formula (I) when $R^1$ and $R^2$ are hydrogen, $R^3$ is methoxy, $R^4$ is hydroxyl and R is a methyl group. One embodiment of the invention encompasses compounds of formula (I) or their pharmaceutically acceptable salts.

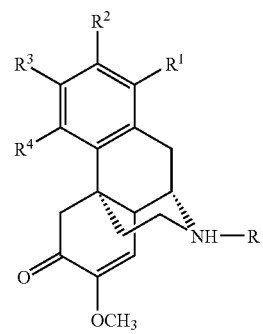

Formula I

In Formula I, the substituents $R^1$, $R^2$, $R^3$, $R^4$ on the benzene ring are independently selected from the group consisting of H, halogen (F, Cl, Br or I), —OH, —NH$_2$, —NO$_2$, —CN, acyl, alkyl, alkoxyl, alkylamino, cycloalkyl, heterocyclyl, heterocyclylalkyl, alkenyl, heteroaryl, heteroarylthio, and heteroarylamino, wherein the named organic substituents have from 1 to 20 carbon atoms.

Each acyl, alkyl, alkoxyl, alkylamino, cycloalkyl, heterocyclyl, heterocyclylalkyl, alkenyl, heteroaryl, heteroarylthio, and heteroarylamino may itself be substituted with one or more radicals independently selected from the group consisting of halogen, N, O, —S, —CN, —N$_3$, —SH, nitro, oxo, acyl, alkyl, alkoxyl, alkylamino, alkenyl, aryl, heterocycloalkyl, and heterocyclyl, wherein these named organic substituents have from 1 to 20 carbon atoms.

R may be a saturated or unsaturated alkyl group that is unbranched, branched or cyclic, having 1 to 20 carbon atoms, or R may be $R^5$—X—CO— wherein X is a bond, or NH, or O; and $R^5$ may be a hydrogen, or a saturated or unsaturated alkyl group that is unbranched, branched or cyclic, having 1 to 20 carbon atoms; or an aromatic group such as an unsubstituted or substituted benzene, naphthalene, pyridine or furan, wherein each alkyl, and aryl, is optionally substituted with or without one or more radicals independently selected from the group consisting of halogen, —S—, —CN, —N$_3$, nitro, oxo, acyl, alkenyl, alkoxyl, alkyl, alkylamino, amino, aryl, cycloalkyl, cycloalkylalkyl, heterocyclyl, heterocyclylalkyl, and hydroxyl; or R may be a sulfonyl group $R^5S(O_2)$—, wherein $R^5$ may be a saturated or unsaturated alkyl group that is unbranched, branched or cyclic, having 1 to 20 carbon atoms; or an aromatic group such as an unsubstituted or substituted benzene, naphthalene, pyridine or furan, etc.; or R may be a sulfonamide group $R^5NS(O_2)$—, wherein $R^5$ may be a saturated or unsaturated alkyl group that is unbranched, branched or cyclic, having 1 to 20 carbon atoms; or an aromatic group such as an unsubstituted or substituted benzene, naphthalene, pyridine or furan, etc., where each alkyl, and aryl, is optionally substituted with or without one or more radicals independently selected from the group consisting of halogen, —S, —CN, —N$_3$, nitro, oxo, acyl, alkenyl, alkoxyl, alkyl, alkylamino, amino, aryl, cycloalkyl, cycloalkylalkyl, heterocyclyl, heterocyclylalkyl, and hydroxyl; wherein $R^5$ may be $R^6$CO— or $R^6SO_2$— wherein $R^6$ may be a saturated or unsaturated alkyl group that is unbranched, branched or cyclic having 1 to 20 carbon atoms; or an aromatic group such as an unsubstituted or substituted benzene, naphthalene, pyridine or furan.

Embodiments of the compounds described above include their pharmaceutically acceptable salts. Further embodiments of the compounds include the corresponding acid addition salts of mineral and organic acids. An illustrative but nonlimiting group of the acid addition salts are those formed with hydrochloric acid, hydrobromic acid, sulphuric acid, phosphonic acid, fumaric acid, tartaric acid, acetic acid, trifluoroacetic acid, lactic acid, succinic acid, citric acid, ascorbic acid, oxalic acid, pyruvic acid, malonic acid or glutaric acid.

Persons of ordinary skill in the art will readily appreciate that substitutions of any of the acids named above with other acids will result in effective salts or acid addition salts of the above described sinomenine compounds and their derivatives. Additional acid substitutions known in the chemical and pharmaceutical arts are very likely to provide therapeutically useful salts of the compounds disclosed herein.

In an additional embodiment, R has the structural formula according to the following;

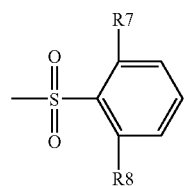

where $R^7$ is a hydrogen atom or a saturated or unsaturated alkyl group that is substituted or unsubstituted, branched or unbranched, or cyclic, and having 1 to 20 carbons or a substituted or unsubstituted ether, ester, amide, amine, thioether or thioester having from 1 to 20 carbon atoms; and $R^8$ is a hydrogen atom, a substituted or unsubstituted alkyl group of 1 to 20 carbon atoms, or a substituted or unsubstituted ether, ester, amide, amine, thioether or thioester having from 1 to 20 carbon atoms.

A further embodiment is defined by R being one of the following,

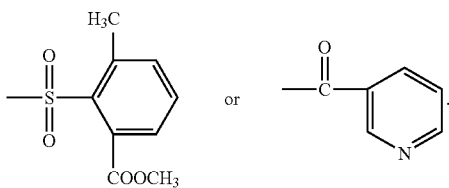

Persons of ordinary skill in the art will readily appreciate that modifications and substitutions may be made in relation to the foregoing R groups, and still provide therapeutically useful compounds. Thus, it will be readily appreciated by persons of ordinary skill in the art that numerous embodiments of the compound of formula I exist that are encompassed by the scope of the invention although they may not be explicitly set forth herein.

The aforementioned sinomenine derivatives may be formulated into numerous pharmaceutical compositions by combining with one or more suitable carriers and/or excipients. Therefore, embodiments of the invention disclosed herein encompass various pharmaceutical compositions suitable for delivering an effective amount of one or more sinomenine derivatives through various routes of administration. These routes of administering the compound or the pharmaceutical composition includes oral/enteric, buccal absorption, colorectal absorption, intravenous, intramuscular, subcutaneous, inhalation and intranasal.

Accordingly, embodiments of pharmaceutical compositions comprising the sinomenine derivatives disclosed herein are pills, tablets, caplets, tablets, liquids, syrups, tonics, lozenges, chewable tablets and gums, sprays, atomized or nebulized compositions, creams, lotions, ointments, emulsions, including microemulsions and nanoemulsions, suppositories, and transdermal patches.

The "human whole blood" model is a physiologically and clinically relevant testing system for predicting the efficacy of an anti-inflammatory agent when administered in vivo to animals and patients. It is believed that compounds that inhibit cytokine release in human whole blood assays are likely to exert this inhibitory effect in vivo. (Hartman et al., Inflamm Res 1995; 44: 269-274; Hermann et al., Journal of Immunological Methods 2003; 275: 69-79; Zhang Y et al: International Immunopharmacology 2004; 4: 1845-1857; Zhang Y et al., J. of Pharmacology and Experimental Therapeutics 2004; 309: 348-355; Lagrelius M et al., Cytokine 2006; 33: 156-165.) Accordingly, identification of effective inhibitors of cytokine release in human whole blood cultures is more likely than not to lead to an effective in vivo or clinical treatment.

The invention disclosed herein also provides a method for inhibiting the release of one or more cytokines in human whole blood comprising the steps of, contacting human whole blood with an amount of a compound of formula I effective to inhibit the release of one or more cytokines in human whole blood cells, and wherein the inhibition of cytokine release is indicative of the compound's anti-inflammatory activity.

In certain instances it is advantageous to induce the cellular release of cytokines in human whole blood in order to assess the effectiveness of putative anti-inflammatory compounds, by quantitating the extent of a compound's inhibition of cytokine release. Cytokine release in whole human blood can be stimulated by several inducers; e.g. release from leukocytes with LPS, from monocytes with zymosan A stimulation (Hartman D A et al: Inflamm Res 1995; 44: 269-274), and from lymphocytes with SEB ("staphylococcal enterotoxin B") (Hermann et al: Journal of Immunological Methods 2003; 275: 69-79).

An additional embodiment of the invention provides for a method for determining whether or not a subject or patient is likely to respond to treatment comprising the administration of the disclosed sinomenine derivatives.

Methods of treating the causes and symptoms of inflammation using one or more of the aforementioned compositions and formulations comprising the sinomenine derivatives disclosed encompass several embodiments of the invention. One embodiment is a method of treating rheumatoid arthritis.

Additional embodiments encompass methods of treating other inflammatory disorders and forms of arthritis. An illustrative and nonlimiting list of such disorders include, e.g., osteoarthritis, systemic lupus erythematosus, gout and similar degenerative disorders, Alzheimer's disease, Parkinson's disease, neurodegenerative disorders, asthma, arrhythmia and inflammation-related pain.

In addition to treatment, it is encompassed herein that the inventive sinomenine derivatives may be adapted as a prophylactic, i.e., preventive, treatment for the above-referenced disorders. The regulation of the dose, formulation and route of administration of the pharmaceutical composition comprising the sinomenine derivatives would likely provide an effective means to prevent inflammation-related disorders, as well as to prevent their re-occurrence.

A non-limiting list of sinomenine derivatives encompassed by the invention is provided for illustrative purposes only. The invention encompasses embodiments of the compound of formula (I) as illustrated by the non-limiting list including 17-propylsinomenine, 17-butylsinomenine, 17-cyclopropylmethylsinomenine, 17-benzylsinomenine, 17-(furan-2'-yl-methyl)-sinomenine, 17-allylsinomenine, 17-cyclopentanylsinomenine, 17-cylclohexanylsinomenine, 17-cycloheptanylsinomenine, 17-(2-phenyl-ethyl)-sinomenine, 17-ethoxycarbonylsinomenine, 17-(2'-oxo-propyl)-sinomenine, 17-(2'-oxo-3'-phenyl-propyl)-sinomenine, 17-methanesulfonylsinomenine, 17-ethanesulfonylsinomenine, 17-propanesulfonylsinomenine, 17-toluenesulfonylsinomenine, 17-(4'-acetylamino)benzenesulfonylsinomenine, 17-(2'-methyl-6'-methoxycarbonyl)benzenesulfonylsinomenine, 17-acetylsinomenine, 17-propanoylsinomenine, 17-butanoylsinomenine, 17-(phenyl)-acetylsinomenine, 17-cyclopropylcarbonyl-sinomenine, 17-(2-Phenylpropanoyl) sinomenine, 17-benzoylsinomenine, 17-(3'-chlorobenzoyl) sinomenine, 17-(4'-methylbenzoyl) sinomenine, 17-(3',5'-dimethylbenzoyl) sinomenine, 17-(2'-hydroxybenzoyl) sinomenine, 17-(3'-hydroxy-2'-methylbenzoyl)sinomenine, 17-(pyridine-3-carbonyl) sinomenine, 17-Furoylsinomenine, 17-(3',4'-difluorobenzoyl)-sinomenine, 17-(4-fluorobenzoyl)-sinomenine, 17-(4-hydroxybenzoyl)-sinomenine, and 17-(4'-acetylamino-benzoyl)-sinomenine.

Another embodiment of the invention relates to methods for synthesizing of 17-substituted sinomenine of formula (I), wherein R is as hereinbefore described. An illustrative example of one synthetic scheme is shown below as Scheme I, and is illustrated by the following steps:

Step (i), reacting sinomenine with BnOBnOH (4-benzyloxybenzyl alcohol) under Mitsunobu conditions to afford intermediate of formula II.

Step (ii), demethylation of the intermediate II using 1-chloroethyl chloroformate as reagent to give 111 (Hitotsuyanagi, Y.; Nishimura, K.; Ikuta, H. Takeya, K.; Itokawa, H. *J. Org. Chem.*, 1995, 60(14), 4549-58)

Step (iii), alkylation, acylation, or sulfonylation of III for the synthesis of intermediate IV;

Step (iv), deprotection of IV with a solution of TFA/DCM (trifluoroacetic acid/dichloromethane) to obtain the compound of formula I (Hamper, B. C.; et al. Tetrahedron Letters, 37(21), 3671-3674. Mergler, M.; et al. *Tetrahedron Letters* 29(32), 4005-8.).

Scheme 1 is meant merely to illustrate, but not limit in any way, the specific process that persons of ordinary skill in the art may use to synthesize 17-substituent sinomenine derivatives. This scheme merely exemplifies a single approach using selected reagents and conditions.

Scheme I

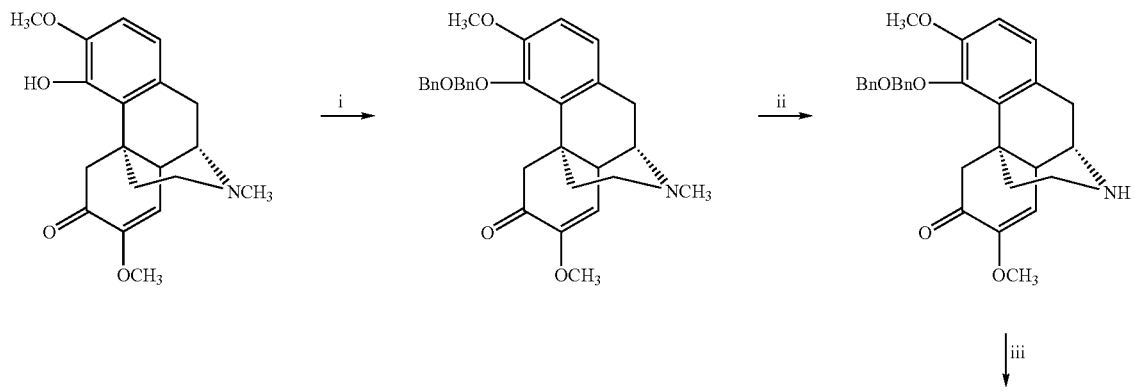

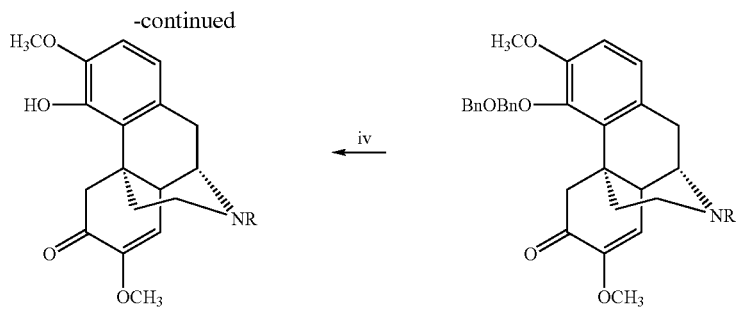

EXAMPLES

The following exemplified embodiments of compounds and methods are included for illustrative purposes only, and not to suggest that the invention is actually limited to what has been exemplified below. Persons of ordinary skill in the art would readily appreciate that the preparation of various sinomenine derivatives encompassed by the disclosure herein may be obtained by making various substitutions of reagent and/or reaction condition. This should be further appreciated by the large number of embodiments disclosed, synthesized and tested herein.

Example 1

Preparation of 17-DemethylBnOBnOsinomenine

Step One: Preparation of BnOBnOsinomenine (Hitotsuyanagi, Y.; Nishimura, K.; Ikuta, H.; Takeya, K.; Itokawa, H. *J. Org. Chem.*, 1995, 60(14), 4549-58.)

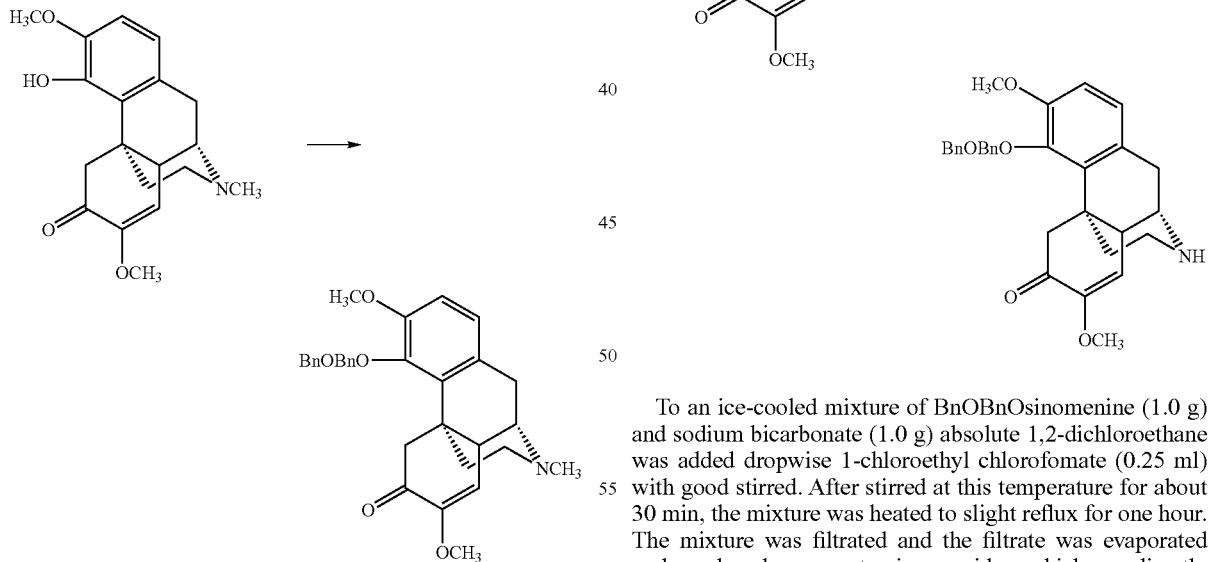

A 25 ml four-necked round-bottomed flask equipped with a magnetic stirrer, was charged a mixture of sinomenine (1.65 g, 5 mmol), PPh$_3$ (3.93 g, 15 mmol), BnOBnOH (3.17 g, mmol) and absolute THF (50 ml). With stirred, the reaction mixture was ice-cooled and diethyl azodicarboxylate (2.61 g, 15 mmol) was added dropwise over a 30 min period. After addition, the mixture was stirred continuously at room temperature for about 12 hr. Removal of THF gave a residue, which was purified by silica gel column chromatography (ethyl acetate, then methanol) to gave a flesh-colored solid. Crystallization from isopropyl ether provided (2.6 g) as a white powder. mp 72° C.; $[\alpha]^{25}_D$ –69.0° (c=0.28 CHCl$_3$); $^1$HNMR (300 MHz, DCCl$_3$) δ: 7.56 (d, 2H, J=8.6 Hz.), 7.48-7.34 (m, 4H), 7.02 (d, 2H, J=8.6 Hz.), 6.77 (dd, 2H, J=8.4 Hz), 5.52 (d, 1H, J=1.5 Hz.), 5.23 (d, 1H, L=10.5 Hz.), 5.11 (s, 2H), 5.01 (d, 1H, J=10.5 Hz), 4.20 (d, 1H, J=16.1 Hz.), 3.83 (s, 3H), 3.53 (s, 3H), 3.18-3.16 (m, 1H), 3.05-2.97 (m, 2H), 2.82-2.73 (m, 1H), 2.49-2.37 (m, 2H), 2.43 (s, 3H), 1.97 (ddd, 1H, J=11.4, 11.4, 4.3 Hz.), 1.87-1.80 (m, 2H).

Step Two: 17-DemethylBnOBnOsinomenine

To an ice-cooled mixture of BnOBnOsinomenine (1.0 g) and sodium bicarbonate (1.0 g) absolute 1,2-dichloroethane was added dropwise 1-chloroethyl chlorofomate (0.25 ml) with good stirred. After stirred at this temperature for about 30 min, the mixture was heated to slight reflux for one hour. The mixture was filtrated and the filtrate was evaporated under reduced pressure to give a residue, which was directly used for the alcoholysis without further purification.

The residue was added to absolute methanol (20 ml) under nitrogen, and the stirred solution was refluxed 1 hr. evaporation of the solvent gave a solid, which was dispensed in 20 ml CHCl$_3$ and neutralized with saturated Na$_2$CO$_3$ solution (5 ml). The organic layer was separated and the water layer was extracted with CHCl$_3$ (10 ml), the combined organic layer was evaporated under reduced pressure to give a solid with light yellow color.

Example 2

Preparation of 17-Propanesulfonylsinomenine

Step One

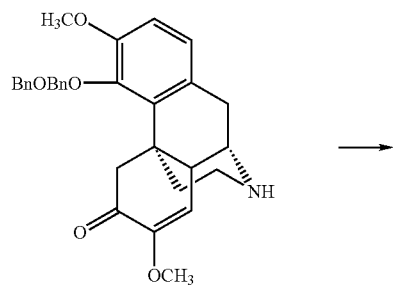

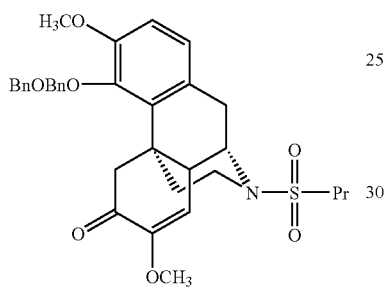

To a stirred solution of 17-demethylBnOBnOsinomenine (100 mg) and triethylamine in $CH_2Cl_2$ (10 ml) was added slowly a solution of propanesulfonyl chloride (50 mg) in $CH_2Cl_2$ (5 ml). After stirred for 5 min, the reaction mixture was evaporated under reduced pressure to give a residue, which is purified by silica gel column (1:2 v/v of ethyl acetate/petroleum ether) to give 17-propanesulfonylBnOBnOsinomenine. $[\alpha]^{25}_D$+210.5° (c=0.06 $CHCl_3$); $^1$HNMR (300 MHz, $DCCl_3$) δ: 7.56 (d, 1H, J=8.7 Hz), 7.48-7.34 (m, 4H), 7.03 (d, 1H, J=8.7 Hz), 6.81 (d, 1H, J=8.7 Hz), 6.78 (d, 1H, J=8.7 Hz), 5.47 (s, 1H), 5.27 (d, 1H, J=10.5 Hz), 5.11 (s, 1H), 5.01 (d, 1H, J=10.5 Hz), 4.37 (s, 1H), 4.21 (d, 1H, J=15.9 Hz), 3.85 (s, 3H), 3.53 (s, 3H), 3.52-3.44 (m, 1H), 3.28-3.20 (m, 1H), 2.97-2.85 (m, 4H), 2.74-2.55 (m, 1H), 2.47 (d, 1H, J=15.9 Hz), 1.94-1.83 (m, 3H), 1.80-1.65 (m, 1H), 107 (t, 3H, J=7.2 Hz).

Step Two

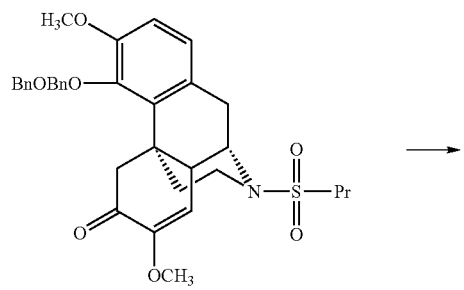

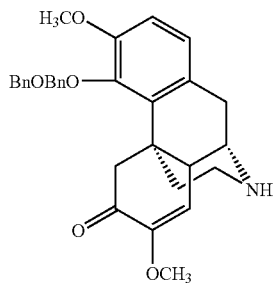

17-propanesulfonylBnOBnOsinomenine (50 mg) was added to a 5% solution of TFA/DCM (5 ml) at room temperature. After stirred for 5 min, 5 ml 10% sodium bicarbonate solution was added slowly. The organic layer was separated, dried with Na2SO4 and then filtrated; the filtrate was evaporated to give a residue, which was purified with silica gel column to provide the title compound in a form of white solid. mp 110.0-113.0° C.; $[\alpha]^{25}_D$+48.2° (c=0.35 $CHCl_3$); $^1$HNMR (300 MHz, $DCCl_3$) δ$_H$, 6.69 (d, 1H, J=8.4 Hz.), 6.57 (d, 1H, J=8.4 Hz.), 6.04 (s, 1H), 5.44 (d, 1H, J=1.8 Hz.), 4.40-4.35 (m, 2H.), 3.84 (s, 3H), 3.56-3.54 (m, 1H), 3.51 (s, 3H), 3.18-3.16 (m, 1H), 3.02-2.95 (m, 3H), 2.91-2.85 (m, 1H), 2.83-2.76 (m, 1H), 2.48 (d, 1H, J=16.0 Hz.), 2.07-2.01 (m, 1H), 1.90-1.82 (m, 3H), 1.08 (t, 3H, J=7.4 Hz.).

Example 3

17-Toluenesulfonylsinomenine

Step One

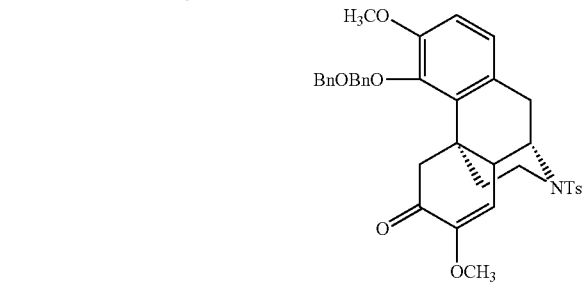

To a mixture of 17-demethylBnOBnOsinomenine (100 mg) and triethylamine (0.1 ml) in dichloromethane (10 ml) was added dropwise a solution of tolunsulfonyl chloride (30 mg) in dichloromethane (5 ml). The mixture was stirred at room temperature for 10 min, and then evaporated under reduced pressure to give crude 17-tolunsulfonylBnOBnOsinomenine, which was directly used for the following process without further purification.

Step Two

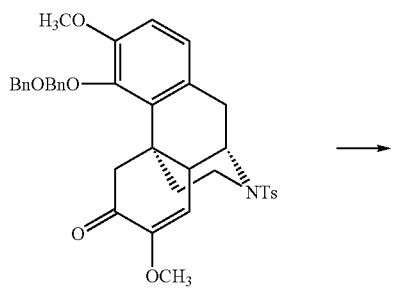

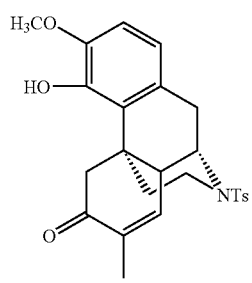

100 mg 17-tolunsulfonylBnOBnOsinomenine, obtained in step, one of this example, was treated with 10 ml 5% TFA/DCM solution as the procedure showed in step two of Example 2 to yield 17-toluenesulfonylsinomenine (50 mg). mp 141.0-143.0° C.; $[\alpha]^{10}_D$+92.4° (c=0.49 CHCl$_3$); $^1$HNMR (300 MHz, DCCl$_3$) δ: 7.74 (d, 2H, J=7.6 Hz.), 7.33 (d, 2H, J=7.6 Hz.), 6.62 (d, 1H, J=8.3 Hz.), 6.38 (d, 1H, J=8.3 Hz.), 6.00 (s, 1H), 5.40 (s, 1H), 4.49 (s, 1H), 4.32 (d, 1H, J=15.70 Hz.), 3.80 (s, 3H), 3.71-3.67 (m, 1H), 3.49 (s, 3H), 3.05-2.99 (m, 1H), 2.84 (s, 1H), 2.74-2.59 (m, 2H), 2.46 (s, 3H), 2.37 (d, 1H, J=15.7 Hz.), 1.97-1.93 (m, 1H), 1.75-1.70 (m, 1H). $^{13}$CNMR (75 MHz, DCCl$_3$) δ: 193.51, 153.11, 145.57, 145.06, 143.77, 138.03, 130.20, 129.03, 128.87, 127.39, 121.36, 119.07, 115.31, 113.30, 109.81, 56.43, 55.25, 51.14, 48.95, 45.13, 40.82, 39.96, 35.57, 30.99, 21.94.

Example 4

Preparation of 17-Cyclopropylmethylsinomenine

Step One

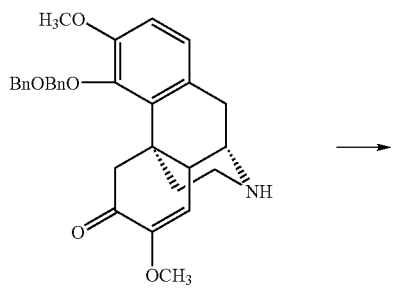

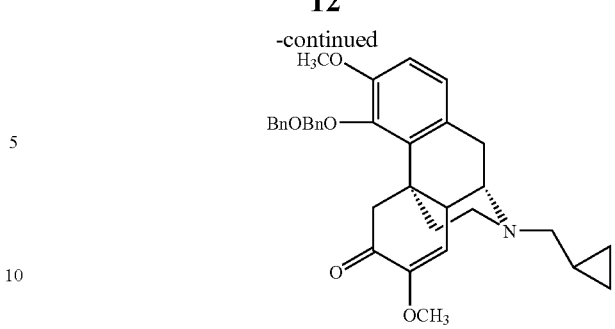

To a solution of 17-demethylBnOBnOsinoemnine (100 mg) in methanol (30 mg) was added cyclopropylmethyl aldehyde (10 ml) and NaBH3CN (50 mg), the reaction mixture was stirred at ambient temperature for 6 hr. removal of the solvent gave a residue, which was dissolved with 20 ml CHCl$_3$ and 10 ml 5% NH4Cl. The organic layer was separated and dried with Na$_2$SO$_4$ and then evaporated under reduced pressure to give the crude 17-cyclopropylmethylBnOBnOsinomenine.

Step Two

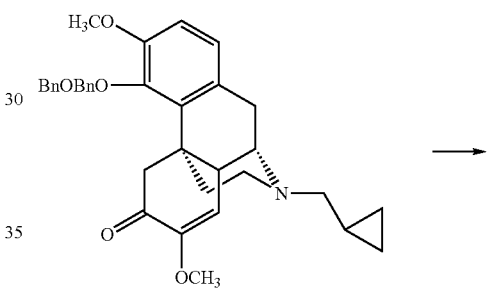

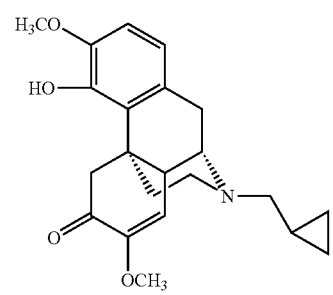

The crude intermediate was treated by 5% TFA/DCM (10 ml) as the procedure of example 2 to yield 17-cyclopropylmethylsinomenine (a white solid). mp: 127.0-127.5° C.; $[\alpha]^2_D$-5.3°(c=0.52, CHCl$_3$); $^1$HNMR (300 MHz, CDCl$_3$) δ: 6.62 (d, 1H, J=8.4 Hz), 6.51 (d, 1H, J=8.4 Hz), 6.09 (s, 1H), 5.49 (d, 1H, J=2.0 Hz), 4.35 (d, 1H, J=15.6 Hz), 3.79 (s, 1H), 3.50 (s, 1H), 3.49-3.42 (m, 1H), 3.04-3.02 (m, 1H), 2.90 (d, 1H, J=18.3 Hz), 2.80-2.76 (m, 1H), 2.73-2.63 (m, 1H), 5.53-2.48 (m, 1H), 2.46 (d, 1H, J=15.6 Hz), 2.35-2.30 (m, 1H), 2.03-1.91 (m, 1H), 1.89-1.80 (m, 1H), 0.90-0.83 (m, 1H), 0.52-0.49 (m, 2H), 0.15-0.11 (m, 2H). $^{13}$CNMR (75 MHz, CDCl$_3$) δ: 194.47, 152.71, 145.27, 145.06, 130.98, 123.21, 118.53, 115.87, 109.29, 60.36, 56.42, 55.15, 55.03, 49.71, 46.20, 46.01, 41.51, 36.36, 25.52, 9.77, 4.47, 4.06.

Example 5

Preparation of 17-Cyclopropylmethylsinomenine-HCl

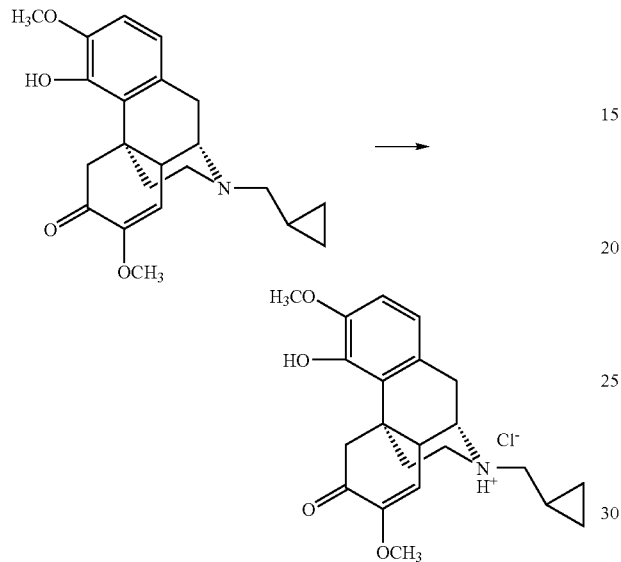

17-cyclopropylmethylsinomenine (50 mg) obtained in Example 4 was dissolved with DCM (2 ml), and dry HCl was introduced to the solution with a glass pipe to produce a white solid as the title compound.

Example 6

Preparation of 17-Cyclopentanylsinomenine

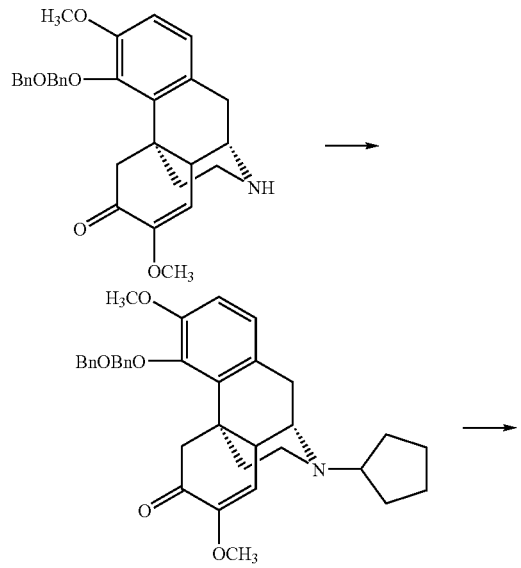

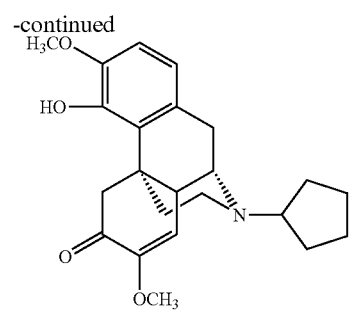

The title compound was prepared starting from cyclopentanone and 17-demethylBnOBnOsinomenine by the procedure showed in Example 4, as a white solid. mp: 180.0-182.0° C.; $[\alpha]^{25}_D$ -69.5° (c=0.48, CHCl$_3$); $^1$HNMR (300 MHz, CDCl$_3$) δ: 6.65 (d, 1H, J=8.3 Hz), 6.55 (d, 1H, J=8.3 Hz), 5.98 (s, 1H), 5.48 (s, 1H), 4.36 (d, 1H, J=15.6 Hz), 3.82 (s, 3H), 3.51 (s, 3H), 3.45-3.41 (m, 1H), 3.07-3.01 (m, 2H), 2.90-2.69 (m, 3H), 2.46 (d, 1H, J=15.6 Hz), 2.05-1.85 (m, 6H), 1.85-1.70 (m, 2H), 1.61 (m, 1H), 1.50-1.40 (m, 2H). $^{13}$CNMR (75 MHz, CDCl$_3$) δ: 194.50, 152.65, 145.29, 145.05, 130.91, 123.15, 118.49, 115.85, 109.30, 63.84, 56.43, 55.15, 53.95, 49.60, 46.15, 45.18, 41.18, 36.45, 32.03, 31.42, 25.03, 24.17, 23.98.

Example 7

Preparation of 17-(2'-Oxo-Propyl)-Sinomenine

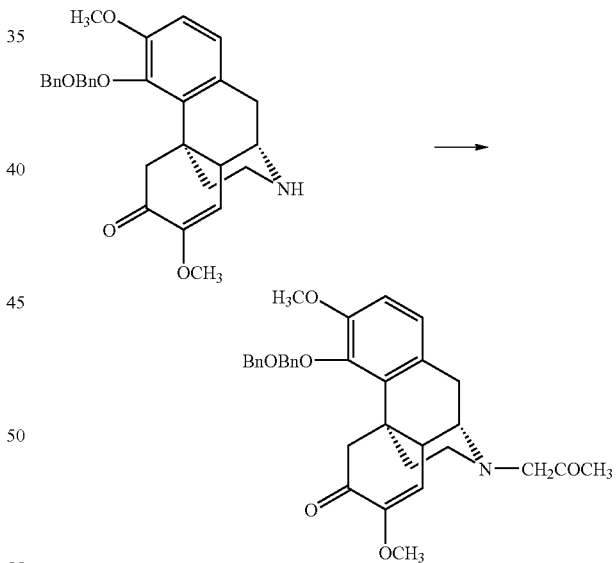

1-Chloroacetone (20 mg) was added to a stirred mixture of 17-demethylBnoBnosinomenine (100 mg) and potassium carbonate (30 mg) in acetone (10 ml), the reaction mixture was heated to reflux for 30 min. after cooling, it was filtrated and then evaporated to remove the solvent. Purification of the residue with silica gel column (1:1 ethyl acetate/petroleum ether) gave 17-(2'-oxo-propyl)-BnOBnOsinomenine as a gummy solid. $[\alpha]^{25}_D$+27.5° (0.11 CHCl$_3$); $^1$HNMR (300 MHz, DCCl$_3$) δ: 7.55 (d, 1H, J=8.7 Hz), 7.48-7.34 (m, 5H), 7.02 (d, 2H, J=8.7 Hz), 6.78 (s, 2H), 5.47 (s, 1H), 5.27 (d, 1H, J=10.8 Hz), 5.11 (s, 2H), 5.01 (d, 1H, J=10.8 Hz), 4.20 (d, 1H, J=15.9 Hz), 3.84 (s, 3H), 3.57-3.3.53 (m, 2H), 3.52 (s, 3H), 3.52-3.35 (m, 1H), 3.27 (m, 1H), 2.94 (s, 2H), 2.76-2.70 (m, 1H), 2.50 (d, 1H, J=15.9 Hz), 2.24 (s, 3H), 1.94-1.83 (m, 1H), 1.87-1.82 (m, 2H).

17-(2'-oxo-propyl)-BnOBnOsinomenine (60 mg) was treated with 5% TFA/DCM (5 ml) by the procedure of example 4 to provide 17-(2'-oxo-propyl)-sinomenine as a white solid. mp 147.2-148.0° C.; $[\alpha]^{25}_D$+53° (c=0.21 CHCl$_3$); $^1$HNMR (300 MHz, CDCl$_3$) δ: 6.65 (d, 1H, J=8.3 Hz), 6.54 (d, 1H, J=8.3 Hz), 5.99 (s, 1H), 5.44 (d, 1H, J=1.5 Hz), 4.36 (d, 1H, J=15.6 Hz), 3.82 (s, 1H), 3.49 (s, 1H), 3.44 (d, 1H, J=17.1 Hz), 3.29 (d, 1H, J=17.1 Hz), 3.25 (m, 1H), 3.12 (s, 1H), 2.98-2.70 (m, 2H), 2.57-2.53 (m, 1H), 2.47 (d, 1H, J=15.6 Hz), 2.21 (s, 3H), 2.18-2.10 (m, 1H), 1.96-1.91 (m, 2H)

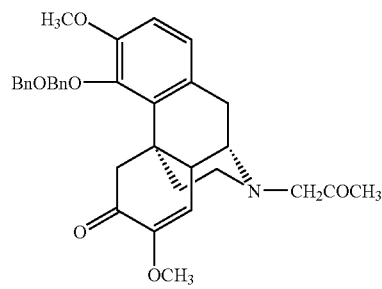

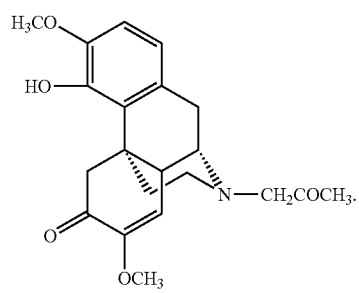

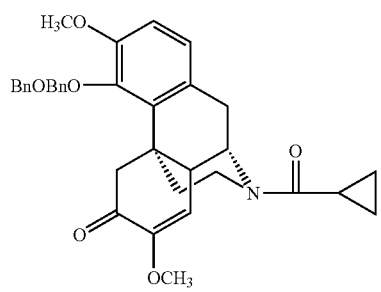

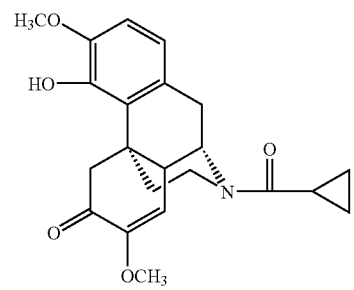

To a mixture of 17-demethyl-BnOBnosinomenine (100 mg) and cyclopropylcarboxylic acid (18 mg) in DCM (10 ml) was added DCC (45 mg), after stirred at room temperature for 6 hr, the reaction mixture was filtrated and then washed with saturated NaHCO$_3$ solution (2×10 ml). The organic layer was dried with Na$_2$SO$_4$ and evaporated to leave a crude solid.

The crude solid was treated directly with 5% TFA/DCM (20 ml) as the procedure of example 2 to yield a white solid. mp>187.0° C.; +144.2°(c 0.22 CHCl$_3$); $^1$HNMR δ: 6.69 (d, 1H, J=8.1 Hz.), 6.54 (d, 1H, J=8.1 Hz.), 6.05 (s, 1H), 5.50 (s, 1H), 5.17 (s, 0.7H), 4.78 (br s, 0.3H), 4.41 (d, 1H, J=15.6 Hz.), 4.04-4.00 (m, 0.7H), 3.84 (s, 3H), 3.54, 3.52 (each s, 0.9, 2.1H), 3.43 (s, 0.3H), 3.25-3.10 (m, 1H), 3.02-2.93 (m, 1H), 2.83 (s, 1H), 2.69 (d, 1H, J=17.7), 2.46 (d, 1H, J=15.6 Hz.), 2.10-2.06 (m, 1H), 1.90-1.80 (m, 1H), 1.75-1.65 (m, 1H), 1.05-1.00 (m, 2H), 0.85-0.70 (m, 2H).

Example 8

Preparation of 17-cyclopropylcarbonylsinomenine

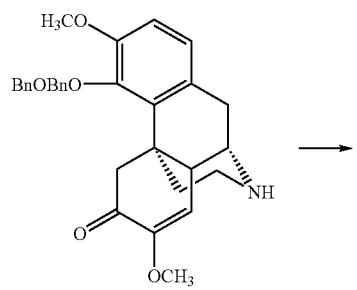

Example 9

Preparation of 17-(3', 5'-Dimethyl-Benzoyl)-Sinomenine

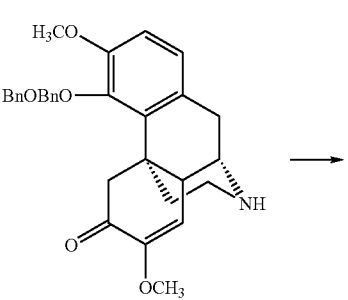

-continued

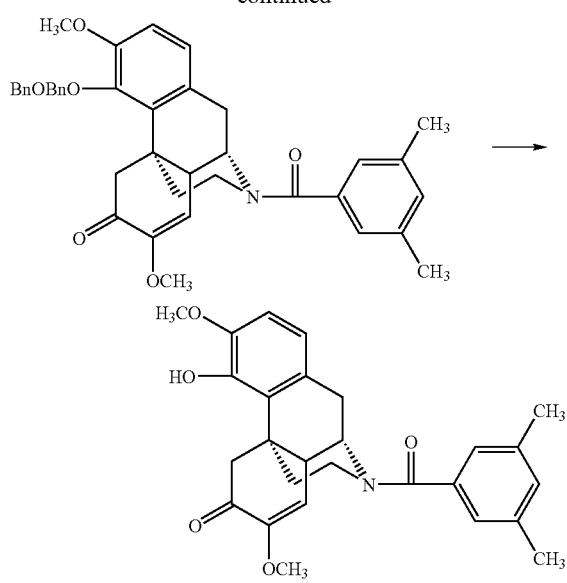

To a mixture of 17-demethylBnOBnOsinomenine (10 mg) and triethylamine (0.05 ml) in DCM (10 ml) was added 3,5-dimethylbenzoyl chloride (50 mg). The reaction mixture was stirred at ambient temperature for about 5 min, then was removed a part of the solvent (about 7 ml). To the residue was treated with 5% TFA/DCM (10 ml), as the procedure of Example 2 to give a residue, which was chromatographed on silica gel column (1:1 ethyl acetate/petroleum ether) to obtain the title compound. Mp 147.2-149.6.

Example 10

Illustrative List of Embodiments of Sinomenine Derivatives

The table below provides a non-limiting list of compounds encompassed by Formula I. Each embodiment is characterized by the number assignment and the structure defining the R group, replacing the methyl group in the parent compound (Table A), the entire structure (Table B), or by delineating the substitutions of $R^1$-$R^4$ and R (Table C). Although the list illustrates 69 distinct embodiments, of formula I, persons of ordinary skill in the art will readily appreciate that the actual number of possible embodiments encompassed by the invention disclosed here, is far greater.

TABLE A

| Compound Number | R | MW |
|---|---|---|
| 1. comparison | —CH$_3$ | 329 |
| 2. comparison | —CH$_3$HCl | 365.5 |
| 3. | 2-hydroxybenzoyl | 435 |
| 4. | 4-methylphenylsulfonyl | 469 |
| 5. | —SO$_2$Me | 393 |
| 6. | —SO$_2$Et | 408 |
| 7. | —SO$_2$Pr | 421 |
| 8. | —Ac | 357 |
| 9. | 3,5-dimethylbenzoyl | 447 |
| 10. | —CO-cyclopropyl | 383 |
| 11. | 3-hydroxy-2-methylbenzoyl | 450 |
| 12. | —COPh | 419 |
| 13. | cyclopentyl | 383 |
| 14. | —COCH$_2$CH$_3$ | 371 |
| 15. | —COCH$_2$CH$_2$CH$_3$ | 385 |
| 16. | —COCH$_2$Ph | 433 |
| 17. | —COCH$_2$O-(2-methylphenyl) | 463 |
| 18. | —COCH(CH$_3$)Ph | 447 |
| 19. | —CO-(2,4-difluorophenyl) | 455 |
| 20. | —CH$_2$-(5-chloro-1-methyl-3-methyl-pyrazol-4-yl) | 457.5 |
| 21. | —CH$_2$COCH$_3$ | 371 |
| 22. | —CH$_2$COOEt | 401 |
| 23. | cyclohexyl | 397 |

TABLE A-continued
| Compound Number | R | MW |
|---|---|---|
| 24. |  | 411 |
| 25. | 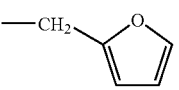 | 395 |
| 26. | —CH₂COPh | 433 |
| 27. | —CH₂CH=CH₂ | 355 |
| 28. | 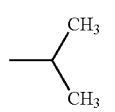 | 357 |
| 29. | —CH₂Ph | 405 |
| 30. | 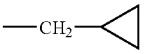 | 369 |
| 31. | —Pr | 357 |
| 32. | -Bu | 371 |
| 33. | 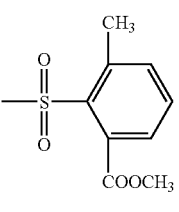 | 527 |
| 34. | 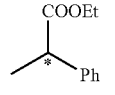 | 437 |
| 35. | 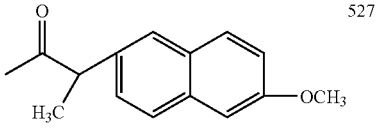 | 527 |
| 36. | 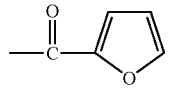 | 409 |
| 37. | 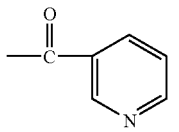 | 420 |
| 38. | 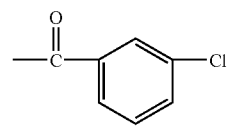 | 453.5 |
| 39. | 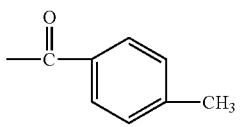 | 433 |
TABLE A-continued
| Compound Number | R | MW |
|---|---|---|
| 40. | 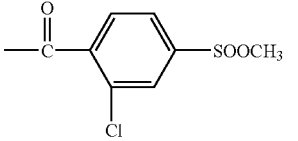 | 531.5 |
| 41. | 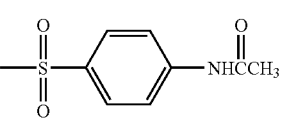 | 512 |
TABLE B
| Compound Number | Compound Structure | MW |
|---|---|---|
| 42. | 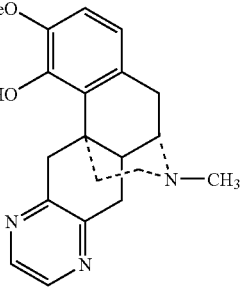 | 337 |
| 43. | 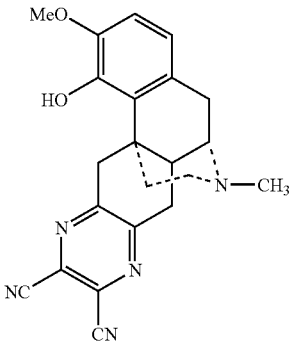 | 387 |
| 44. | 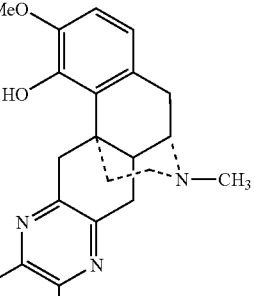 | 387 |

TABLE B-continued

| Compound Number | Compound Structure | MW |
|---|---|---|
| 45. | | 401 |
| 46. | | 317 |
| 47. | | 477 |
| 48. | | 499 |
| 49. | 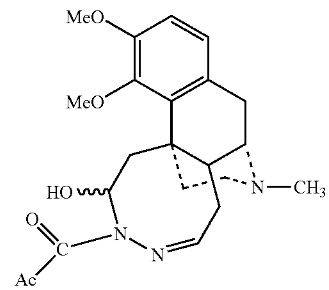 | 415 |
| 50. | 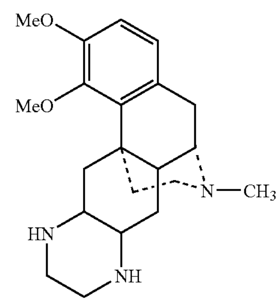 | 343 |
| 51. | 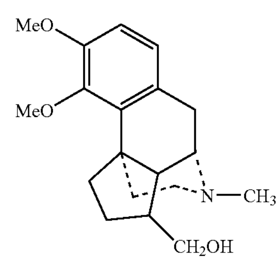 | 315 |
| 52. | 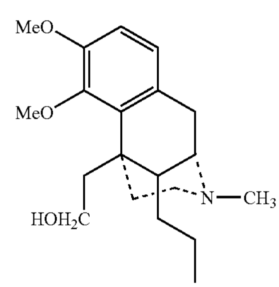 | 335 |
| 53. | 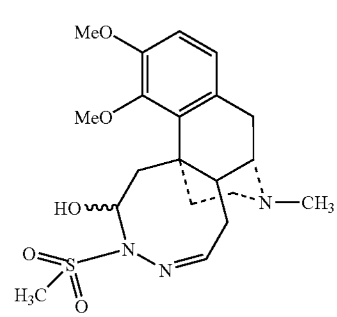 | 435 |

TABLE B-continued

| Compound Number | Compound Structure | MW |
|---|---|---|
| 54. | (structure: dimethoxy tetracyclic scaffold with N—CH₃, HO, and N—N=linked benzoyl group) | 449 |

TABLE C (Core structure: tetracyclic scaffold with substituents R¹, R², R³, R⁴ on aromatic ring, ketone (O=), OCH₃, and NH—R)

| Compound 55 | R¹ = R² = H, R³ = OCH₃, R⁴ = OH, R = CO—CONEt₂ |
| Compound 56 | R¹ = R² = H, R³ = OCH₃, R⁴ = OH, R = (ketone-CH₂CH₂-piperidine) |
| Compound 57 | R¹ = R² = H, R³ = OCH₃, R⁴ = OH, R = (sulfonyl-CH₂CH₂-piperazine) |
| Compound 58 | R¹ = R² = H, R³ = OCH₃, R⁴ = OH, R = (sulfonyl-CH₂-N(CH₃)₂) |
| Compound 59 | R¹ = R² = H, R³ = OCH₃, R⁴ = OH, R = (sulfonamide-NH-phenyl) |
| Compound 60: | R¹ = R² = H, R³ = OCH₃, R⁴ = OH, R = (ester-O-CH₂-phenyl) |

TABLE C-continued (Same core structure)

| Compound 61: | R¹ = R² = H, R³ = OCH₃, R⁴ = OH, R = (amide-NH-ethyl) |
| Compound 62: | R¹ = R² = H, R³ = OCH₃, R⁴ = OH, R = (sulfonyl-N-benzoyl) |
| Compound 63: | R¹ = R² = H, R³ = OCH₃, R⁴ = OH, R = (amide-NH-CH₂-methylenedioxyphenyl) |
| Compound 64: | R¹ = Br, R² = H, R³ = OCH₃, R⁴ = OH, R = (sulfonyl-p-tolyl) |
| Compound 65: | R¹ = Br, R² = Br, R³ = OCH₂Ph, R⁴ = OH, R = (sulfonamide-NH₂) |
| Compound 66: | R¹ = R² = H, R³ = OCH₃, R⁴ = OH, R = (amide-NH—OH) |
| Compound 67: | R¹ = R² = H, R³ = OCH₂Ph, R⁴ = OH, R = (CH₂—CF₃) |
| Compound 68: | R¹ = R² = H, R³ = OCH₃, R⁴ = OH, R = (2-pyrimidinyl) |
| Compound 69: | R¹ = R² = H, R³ = OCF₃, R⁴ = OH, R = (keto-phenyl) |

Example 11

Preparation of a Combinatorial Library of Sinomenine Derivatives

The invention encompasses combinatorial libraries where the member compounds have the following structures:

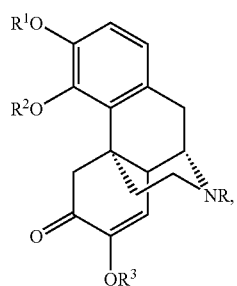

or more specifically

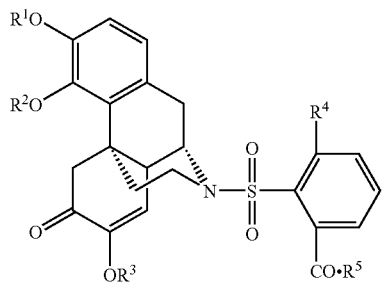

and/or

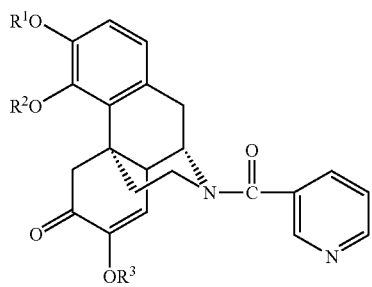

Chemical synthesis in traditional way is the process of a single step and single reaction. The concept is that a compound is generated from a chemical reaction. For example in the figure shown below, the reaction between $R_1COOH$ and $R_2NH_2$ under proper conditions will generate a new and single compound. However, the cost of this traditional approach is high and the efficiency is low.

The concept of combinatorial chemistry is the reactions between multiple species of $R_1COOH$ and $R_2NH_2$. These reactions can yield multiple compounds for testing. Indicated in FIG. 1 the reactions between 50 $R_1COOH$ and 50 $R_2NH_2$ produce a library containing 2500 amides. Using this approach the efficiency is much higher than traditional chemical synthesis.

FIG. 1. Conventional Chemistry and Combinatorial Chemistry

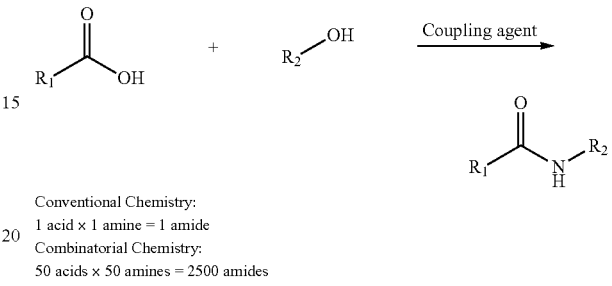

Conventional Chemistry:
1 acid × 1 amine = 1 amide
Combinatorial Chemistry:
50 acids × 50 amines = 2500 amides There are two basic methods for combinatorial chemistry: Solid Phase Synthesis and Solution Phase Synthesis.

Solid Phase Synthesis:

In brief, small molecules are chemically bound to polymer materials such as polystyrene. Because the polymer materials can be expanded in organic solvents, the chemical agents diffuse into the polymer materials and react with the chemical molecules. After completion of chemical reaction, impurities and other unneeded compounds can be filtered or washed away. Targeted new molecules or compounds can be extracted using proper chemical approaches. The advantages of solid phase synthesis is to avoid the traditional ways such as using column or distillation for purifying the products. The most famous method in this type of synthesis is so-called "Mix-and-Split" approach. Using this approach, many chemical reaction steps can be eliminated. For instance, To establish a chemical library with compounds which have three modified positions (50×50×50 library), 150 reactions will be needed for a library with 125000 compounds. However, if traditional chemical synthesis or parallel synthesis are used 125000 chemical reactions will be needed for the library with 125000 compounds.

Solution Phase Synthesis:

Parallel synthesis is the major method in this category. The concept of solution phase synthesis is that multiple chemical reactions are occurred based on traditional chemical reaction. For instance, in order to obtain a library with 2500 compounds using 50 acids and 50 amines, 2500 chemical reactions will be needed. The advantages of this approach are that less time will be spent to optimize the experimental conditions, the amount of compound production is bigger and easily to handle. The disadvantage is less efficient. Combinatorial chemistry approaches have been widely used for seeking new compounds; however, combinatorial chemistry has not been used to modify the leading structures from traditional Chinese herbal medicines. We designed the specific combinatorial chemical synthetic approach to build up sinomenine derivatives library, indicating in the Scheme as below: (Scheme 1):

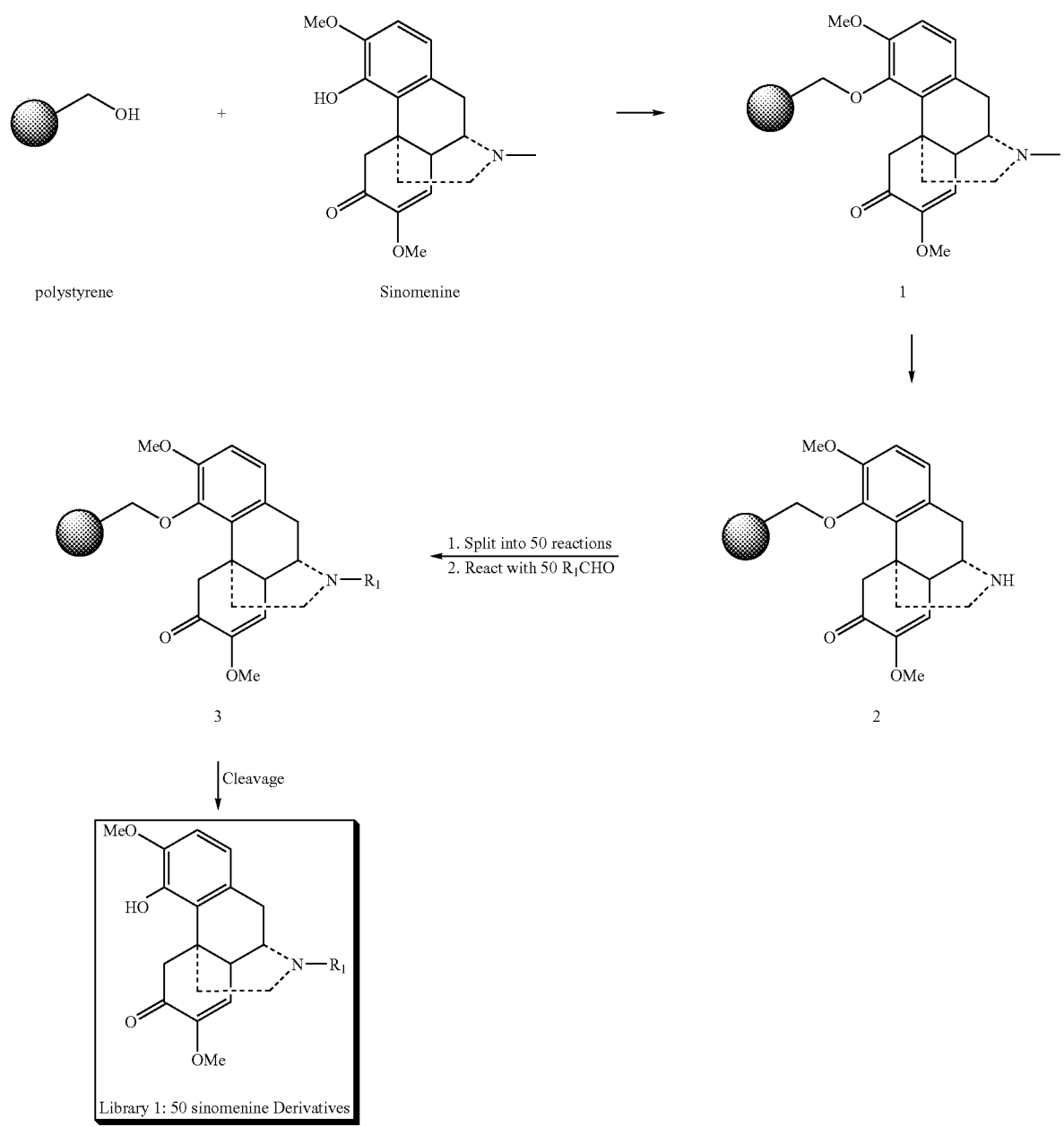

Scheme 1. 50 Compound Library Synthesis

- Sinomenine reacts with polymer material such as polyvinyl benzene under proper chemical condition; an intermediate (1) will be formed due to the combination of sinomenine and polyvinyl benzene via convalent bond.
- N-methyl is selectively eliminated and intermediate (2) is obtained.
- Intermediate (2) is placed into 50 different reactors and reacts with 50 aldehyde ($R_1CHO$, here $R_1$ can be different chemical group), intermediate (3) is obtained via reductive amination reaction.
- In proper condition, sinomenine derivative can be cleaved from polymer material and a library with 50 sinomenine derivatives will be obtained. If 500 $R_1CHO$ are used a library with 500 sinomenine derivatives will be established. These compounds can be used for further screening of its bioactivities.

Intermediate (3) can be used for other chemical reactions for new chemical compound library, indicated as Scheme 2 below. For example, the carbonyl of intermediate (3) can be selectively reduced and intermediate (5) is obtained. Then using "Mix-and-Split" approach, the intermediate (5) reacts with 50 $R_2X$ to yield sinomenine derivatives (6). The final compound is cleaved from polymer material and a library with 2500 sinomenine derivatives is established.

Scheme 2: 2500 Compound Library Synthesis

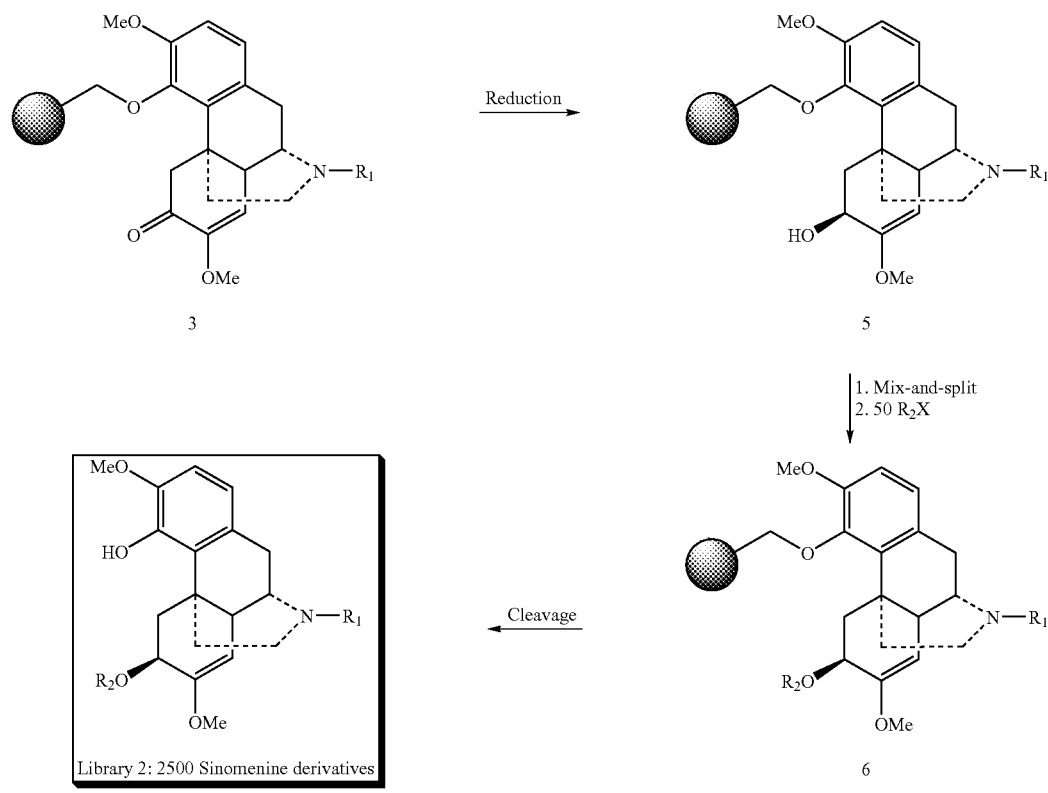

Example 12

Bioactivity

The bioactivities of the sinomenine derivatives were assessed by measuring the inhibition of cytokine release of induced by lipopolysaccharide (LPS) using human whole blood culture. Cytokine release in whole human blood can also be stimulated by zymosan A (Hartman D A et al: Inflamm Res 1995; 44: 269-274), and with SEB ("staphylococcal enterotoxin B") (Hermann et al: Journal of Immunological Methods 2003; 275: 69-79). The levels of four cytokines which have roles in rheumatoid arthritis were examined: TNF-α, IL-1, IL-6 and IL-8. Because TNF-α is the most important mediator responsible for pathology of rheumatoid arthritis, the magnitude of the inhibition by tested compounds of TNF-α release was used to identify key compounds for further characterization such as the inhibition of the release of IL-1, IL-6 and IL-8 and their median inhibitory concentration ($IC_{50}$).

It is believed that compounds that inhibit cytokine release in human whole blood assays are likely to exert this inhibitory effect in vivo. (Hartman et al., Inflamm Res 1995; 44: 269-274; Hermann et al., Journal of Immunological Methods 2003; 275: 69-79; Zhang Y et al: International Immunopharmacology 2004; 4: 1845-1857; Zhang Y et al., J. of Pharmacology and Experimental Therapeutics 2004; 309: 348-355; Lagrelius M et al., Cytokine 2006; 33: 156-165.) Accordingly, identification of inhibitors of cytokine release in human whole blood cultures is likely to lead to an effective clinical treatment.

For example, the model of human whole blood cytokine release has been employed to characterize various patient groups over the years, e.g. multiple sclerosis (Beck et al., 1988 Acta Neurol. Scand. 78, 318-323.; Chofflon et al., 1991, Schweiz. Arch. Neurol. Psychiatr. 142, 107-112; 1992, Eur. Cytokine Netw. 3, 523-531.), leishmaniasis (Frankenburg and Klaus, 1991), rheumatoid arthritis (Zangerle et al., 1992, Cytokine 4, 568-575), sepsis (Volk et al., 1991, Behring Inst., 208-215.; Ertel et al., 1993, Surgery 114, 243-250 (discussion 250-1); Ertel et al., 1994, Arch. Surg. 129, 90-97 (discussion 97-8) 1994); carcinoma (Elsasser-Beile et al., 1993a,b), HIV infection (Hartung et al., 1998, arenfect. Dis. 178, 686-692.) and borreliosis (Diterich et al., 2001). The method also proved to be valuable for ex vivo monitoring of inflammation and immunomodulatory treatments, e.g. in healthy volunteers treated with granulocyte colony-stimulating factor (G-CSF) (Hartung et al., 1995, 1999; von Aulock et al., 2000) or IL-10 (Chemoff et al., 1995, J. Immunol. 154, 5492-5499) or patients treated with granulocyte-macrophage colony-stimulating factor (Hartung et al., 2000).

1. In Vivo Methodology

Formulation

Sinomenine derivatives are assessed as a stable active pharmaceutical ingredient that can be formulated with various inactive materials such as starch, gelatin and etc. to form tablets and/or capsules for oral dosing. In experiments testing bioactivities of sinomenine derivatives in vivo, sinomenine derivatives will be prepared at final concentrations of 30 mg/ml, prepared in a 2% Tween 80 and 0.5% Methylcellulose vehicle for oral administration using in rats. In addition, sinomenine derivatives are soluble in water or buffer-based solvents that encompass many solutions presently used clinically. For example, D5W (Dextrose 5% in water), saline, glucose, phosphorate buffer and etc. Using those solvents, sinomenine derivatives are able to be formulated into injectable form for intravenous injection or infusion as well as subcutaneous and intramuscular administration.

Animal Experimental Protocols

The anti-inflammatory effects of the disclosed and claimed sinomenine derivatives are assessed in vivo using animal arthritis models—e.g., adjuvant-induced arthritis in rats and collagen-induced arthritis in mice.

Adjuvant-Induced Arthritis in Rats

Arthritis are induced in male Lewis rats by intradermal injection of 0.1 ml Freund's Adjuvant-Complete (Signa-Aldrich, Saint Louis, Mo.) via the base of the tail. After eight days the animals develop arthritis and are scored according to published methods. (Zhang, et al: International Immunopharmacology 2004; 4: 1845-1857). Then animals will be assigned randomly to two groups, each group will have at least 6 rats: (1) rats treated with sinomenine derivatives at final concentration of 30 mg/ml, prepared in 2% Tween 80 and 0.5% Methylcellulose vehicle (orally, twice daily at 1 mg/kg), and (2) control group (Tween 80 and 0.5% Methylcellulose vehicle alone). During 21 days of treatment, the effects of the treatment will be assessed by daily monitoring the rear limbs for swelling and erythema of the hindpaws (zhang et al: International Immunopharmacology 2004; 4: 1845-1857). Blood samples will be taken from a peripheral vessel at day 5, day 10 and day 21 for plasma levels of TNF-α, IL-1, IL-6 and IL-8. Animals will be terminated using CO2 after the 21 day treatment. Necropsy will be performed, tarsal joints and synovial tissue of tarsal joints will be removed for histology examination.

Collagen-Induced Arthritis in Mice

Bovine type II collagen solution is maxed with 00.1 M acetic acid and Freund's complete adjuvant (Signa-Aldrich, Saint Louis, Mo.) in a 2:1:3 ratio by POLYTRON (KINEMATICA, Switzerland) to make 1 mg/ml type II collagen emulsion. DBA1/J mince will be injected intradermally with 0.1 ml emulsion at the base of the tail. Twenty-one days after this, the mice will be boosted with 100 μg of bovine type II collagen in Incomplete Freund's Adjunvant. Whether arthritis will be developed in a mouse determining by previously published 4 grades (Wada et al: European Journal of Pharmacology 2005; 506: 285-295): when the grade on either hind paw is greater than 3 the day will be designates as day 0 and the mouse will orally received daily at 100 mg/kg of sinomenine derivatives (prepared in 2% Tween 80 and 0.5% Methylcellulose vehicle) for 21 days. Two groups of mice (n=12 for each group) will be used for the study: treated and control animals (2% Tween 80 and 0.5% Methylcellulose vehicle alone). During the 21 day treatment, the severity of arthritis will be assessed daily using the same scoring system). All animals will be sacrificed using $CO_2$ at 21 day of the treatment all four paws of each animal will be collected for histology examination.

2. Preparation of Human Whole Blood Culture for Assays of Cytokine Release

Human blood sample (~20 ml) was taken from a peripheral venous (10 ml) of a healthy volunteer (Male, 20-50 years old, nonsmoker) using sterile endotoxin-free ethylenediaminetetraacetic (EDTA) tube and was immediately processed. The blood samples were divided into three different experimental conditions (groups): control, stimulating with LPS alone and LPS plus testing compound. Each group contained five blood samples from different individuals. In control group, 100 μl of whole blood sample were diluted with 900 μL of RPMI 1640 in 24 wells plate. In LPS only group or LPS plus testing compound group, 100 ul of whole blood were diluted with 1 μl testing compound or DMSO and 889 ul of RPMI 1640 (RPMI 1640 was consisted of 25 mM Hepes supplemented with 100 U/mL penicillin, 100 μg/mL streptomycin, 4 mM 1-glutamine, and 10% fetal calf serum) All samples from the three groups were incubated in 37° C. and 5% $CO_2$ for 15 minutes, then 10 μl LPS (1 μg/ml) was added into these samples except samples of control group, and was kept in 37° C. and 5% CO2 for 6 h. The samples were placed on ice for 3 minutes and centrifuged for 10 min at 4° C. and 1500 g. The supernatants of the whole blood culture were taken and kept at −80° C. for analysis of TNF-α, IL-1, IL-6 and IL-8. The compositions of each group for the whole blood culture are listed in Table as below:

|  | Control | LPS Only | LPS + Testing compound |
|---|---|---|---|
| Whole Blood(μl) | 100 | 100 | 100 |
| RPMI1640(μl) | 900 | 889 | 889 |
| DMSO(μl) | — | 1 | — |
| 1 μg/ml LPS(μl) | — | 10 | 10 |
| Testing compound (ml) | — | — | 1 |

Figure 1B:
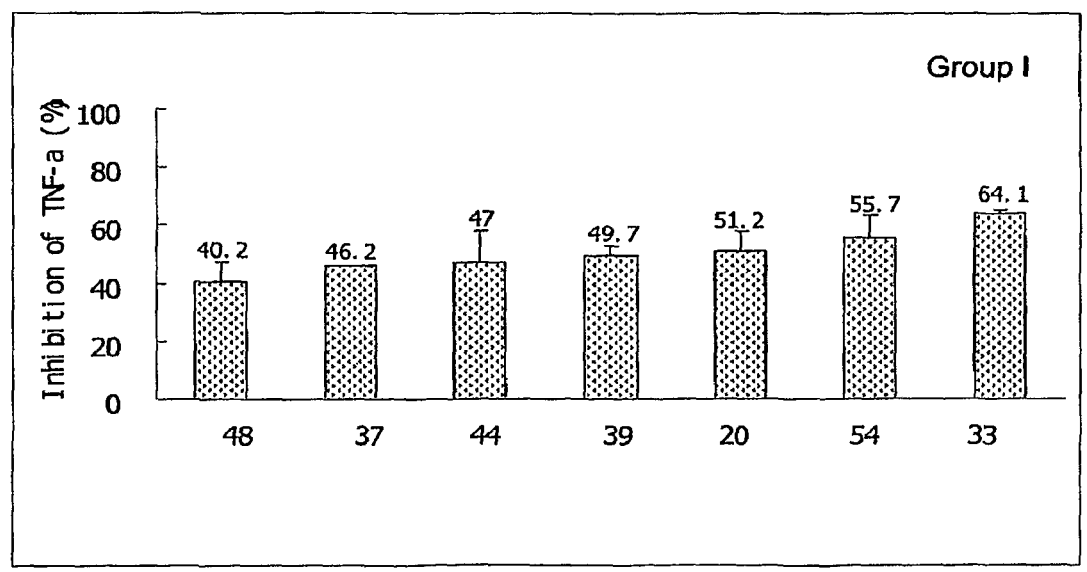
FIG. 1B. Data from Group I are presented as percent inhibition seven of the most effective tested compounds on LPS-induced increase of TNF-α concentration compared to LPS-only control samples.

3. Identification of Candidate Sinomenine Derivatives by the Inhibition of TNF-α Release Assay in Human Whole Blood Culture The samples from above described protocol were used to determine the release of TNF-α from whole blood culture induced by LPS stimulation and the inhibition by each of 22 tested compounds on the LPS-induced TNF-α production. The TNF-α production was assessed using human TNF-α Enzyme Immunometric Assay Kit (Lot. 235123) from R&D Systems (MN, USA), the detail methods are described as the instruction of the Kit. The concentration of LPS-induced TNF-α production in whole blood culture was 884.2±329.8 pg/ml. These 22 compounds were divided into three groups according to their inhibition potencies on the LPS-induced TNF-α production:

Group I: The tested compounds that inhibited LPS-induced TNF-α release greater than 40%, were identified and defined as "key compounds" for further characterization. Seven tested compounds reduced the concentration of LPS-induced TNF-α from 884.2±329.8 pg/ml to less than 530 pg/ml. The ranges of inhibitions of the tested compounds on LPS-induced TNF-α production were from 40.2% to 64.1%. These compounds are #20, #33, #37, #39, #44, #48 and #54. FIGS. 1A and 1B demonstrate the inhibitions of these compounds on the absolute levels of LPS-induced TNF-α productions and the percentage of the inhibitions (bar graphs are arranged by the order of potency).

Figure 2A:
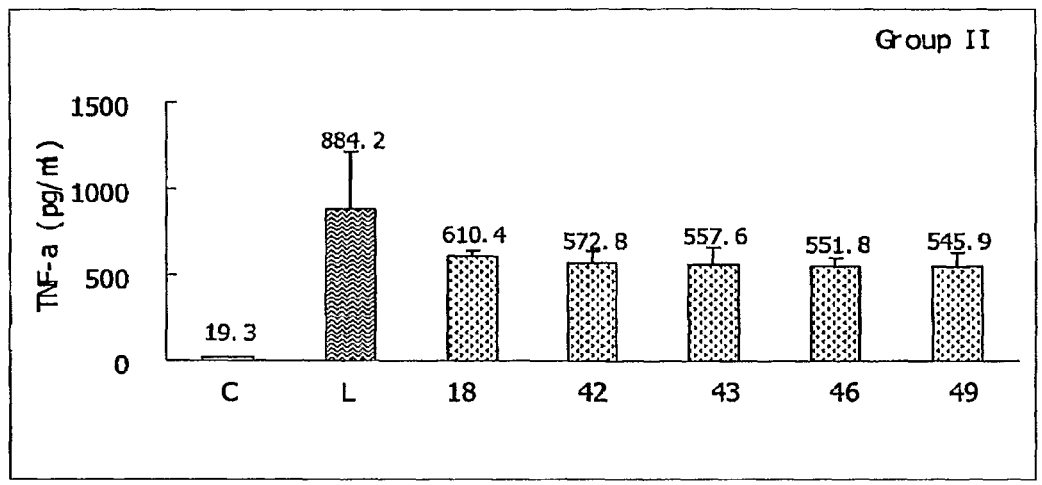
FIG. 2A. The inhibition of TNF-α production in human whole blood culture by five testing compounds of Group II (concentration: $10^{-5}$ mol/L), which were incubated in the presence of LPS (concentration: 10 ng/ml) for 6 h. C: Control (without LPS), L: LPS alone. Data are presented as absolute values. Mean±SD. n=2. Group II, TNF-α level: 530±610 pg/ml: #18, #42, #43, #46 and #49.
Figure 2B:
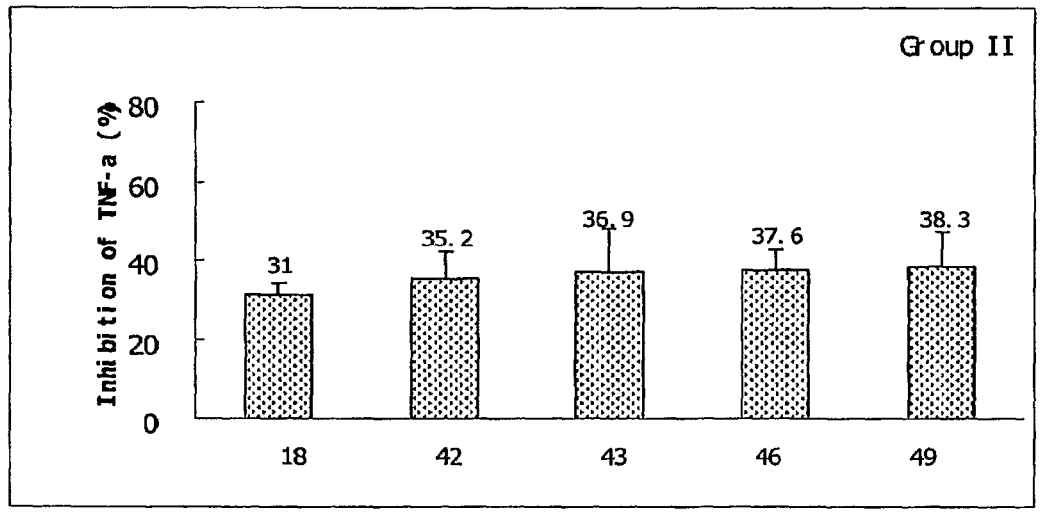
FIG. 2B. Data from Group II are presented as percent inhibition of five tested compounds on LPS-induced increase of TNF-α concentration compared to LPS-only control samples.

Group II: Five tested compounds inhibited LPS-induced TNF-α production less than 40% but greater than 30% compared to LPS alone human whole blood samples. The concentration of LPS-induced TNF-α was reduced from 884.2±329.8 pg/ml to 530 pg/ml-650 pg/ml. The inhibition range of these compounds on LPS-induced TNF-α production was from 31% to 38.3%. These compounds are #18, #42, #43, #46 and #49. FIGS. 2A and 2B demonstrate the inhibition of these compounds on the absolute levels of LPS-induced TNF-α productions and the percentage of the inhibitions (bar graphs are arranged by the order of potencies).

Figure 3A:
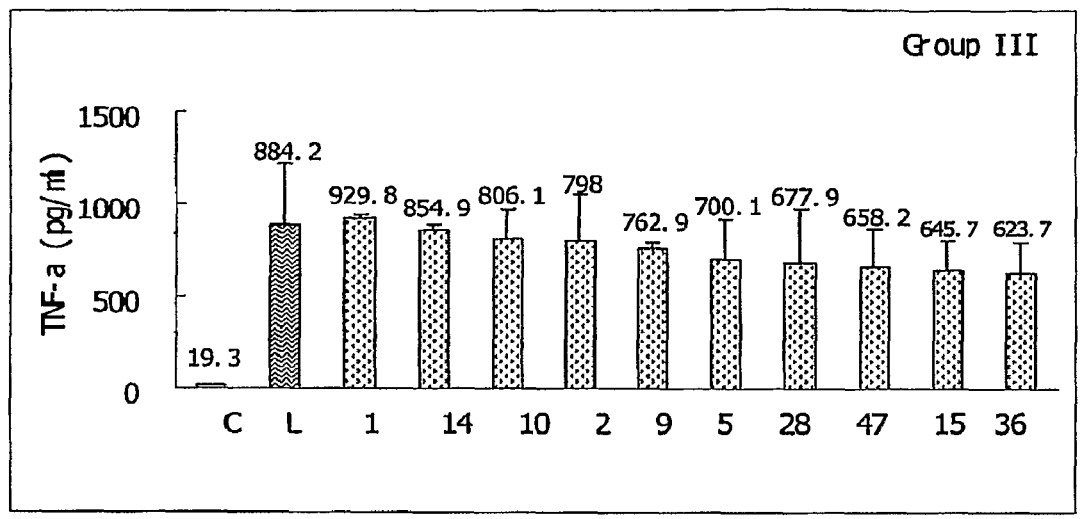
FIG. 3A. The inhibition of TNF-α production in human whole blood culture by ten testing compounds of Group III (concentration: $10^{-5}$ mol/L), which was incubated in the presence of LPS (concentration: 10 ng/ml) for 6 h. C: Control (without LPS), L: LPS alone. Data are presented as absolute values. Mean±SD. n=2. Group III: TNF-α level >610 pg/ml: #1, #2, #5, #9, #10, #14, #15, #28, #36 and #47.
Figure 3B:
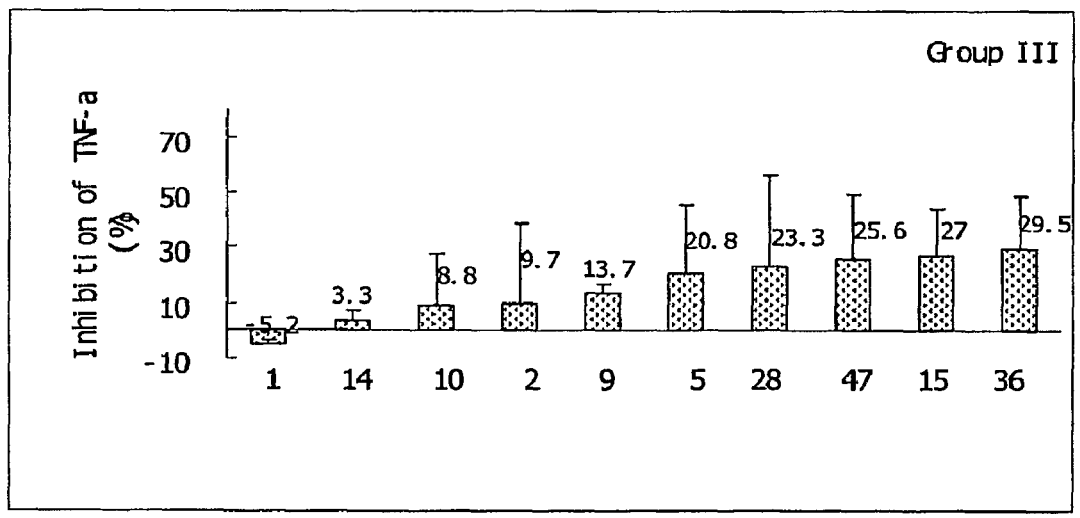
FIG. 3B. Data from Group III are presented as percent inhibition of ten tested compounds on LPS-induced increase of TNF-α concentration compared to LPS-only control samples.

Group III: Ten tested compounds were in this group and these compounds only inhibited the production of LPS-induced TNF-α less than 30%. The range of inhibitions of these compounds on LPS-induced TNF-α production was from 29.5% to −5.2%. These compounds are #1, #2, #5, #9, #10, #14, #15, #28, #36 and #47. FIGS. 3A and 3B demonstrate the inhibitions of these compounds on the absolute levels of LPS-induced TNF-α productions and the percentage of the inhibitions (bar graphs are arranged by the order of potency).

Because TNF-α plays a major role in rheumatoid arthritis and other inflammatory related diseases, thus, those compounds which inhibited LPS-induced TNF-α production by greater than 40% have been used for further studied to determine their median inhibitory concentration ($IC_{50}$) on LPS-induced TNF-α production and other three cytokines IL-1, IL-6 and IL-8. Since compounds #54 and #44 we obtained were mixed chemical isomers, these two compounds have been excluded from the $IC_{50}$ experiments. Five concentrations of the compounds (#20, #33, #37, #39, and #48) were tested: $10^{-9}$, $10^{-8}$, $10^{-7}$, $10^{-6}$, $10^{-5}$ and $10^{-4}$ Molar/L. The parent compound, sinomenine, was used as a control. The $IC_{50}$ was determined by program calcdemo.

4. The $IC_{50}$ of 5 Key Compounds for LPS-Induced TNF-α Production

Figure 4:
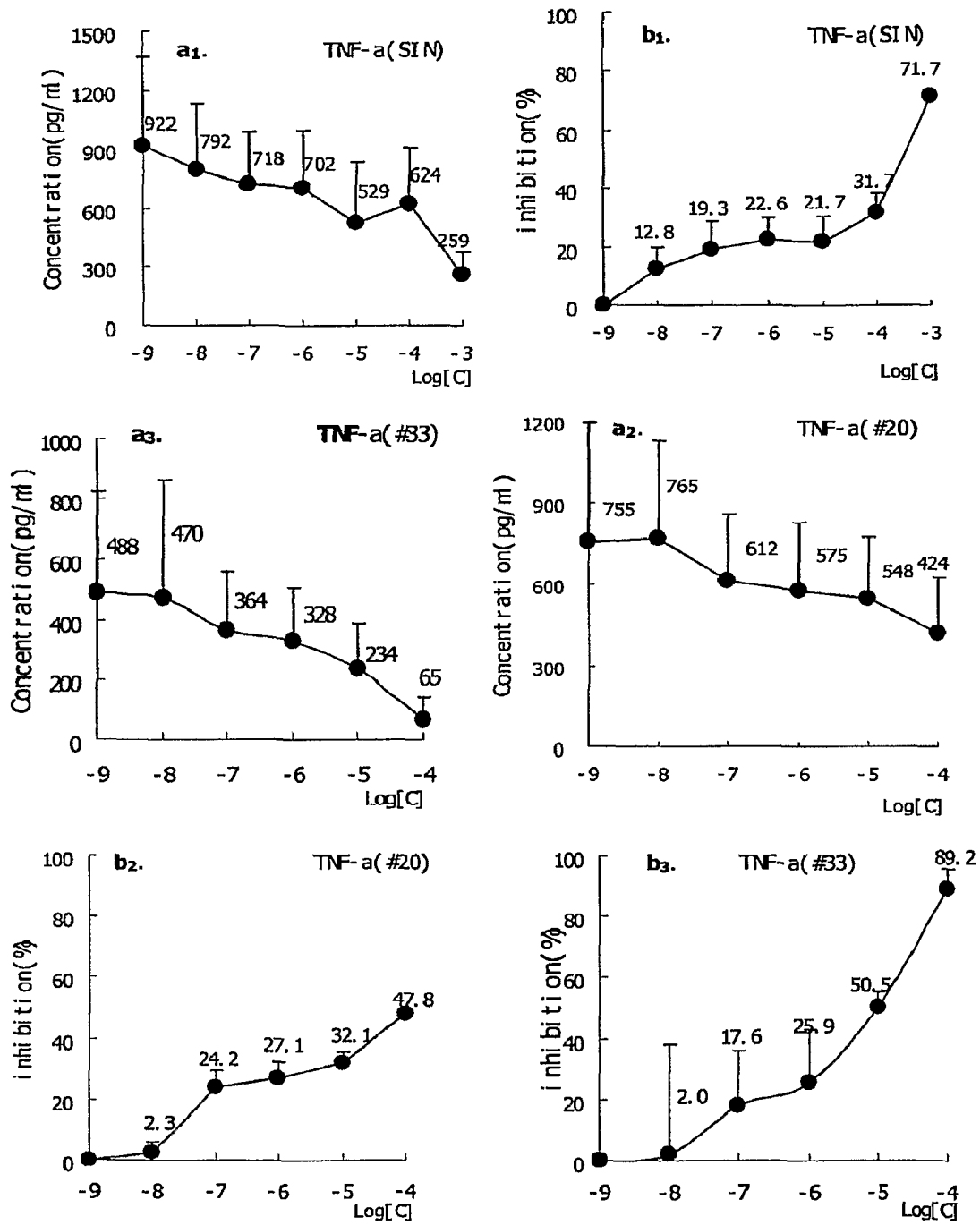
FIG. 4. The $IC_{50}$ of 5 Key Compounds for LPS-induced TNF-α Production.

FIG. 4 demonstrates the dose response curve of 5 key compounds that inhibit LPS-induced TNF-α production in human whole blood culture (concentration: $10^{-9}$-$10^{-5}$ mol/L). The blood samples were incubated in the presence of LPS (concentration. 10 ng/ml) for 6 h. Sinomenine (SIN) was used as control. Because all tested compounds including SIN had no effect at concentration of $10^{-9}$ on LPS-induced TNF-α production, the levels of LPS-induced TNF-α production at $10^{-9}$ of tested compounds in the figures were equivalent to the levels of TNF-α in blood samples with LPS alone. Data in panel a of the figures ($a_1$-$a_6$) present the absolute values of TNF-α; data in panel b ($b_1$-$b_6$) present the percentage inhibition of the tested compounds on LPS-induced TNF-α production. All data were Mean±SD (n=6).

The $IC_{50}$ of the five key compounds that inhibit LPS-induced TNF-α production was determined and summarized in the table as below:

3) Each well was washed by filling wash buffer (600 μL) using an autowasher. The liquid was completely removed at each step to ensure good performance. This process was repeated four times for a total of five washes.

4) 200 μL of Ellman's reagent was added to each well and the plate was covered with a piece of dark paper, incubated for 4 hours at room temperature with gentle shaking.

5) The optical density of each well was determined using a microplate reader set to 412 nm.

Figure 5:
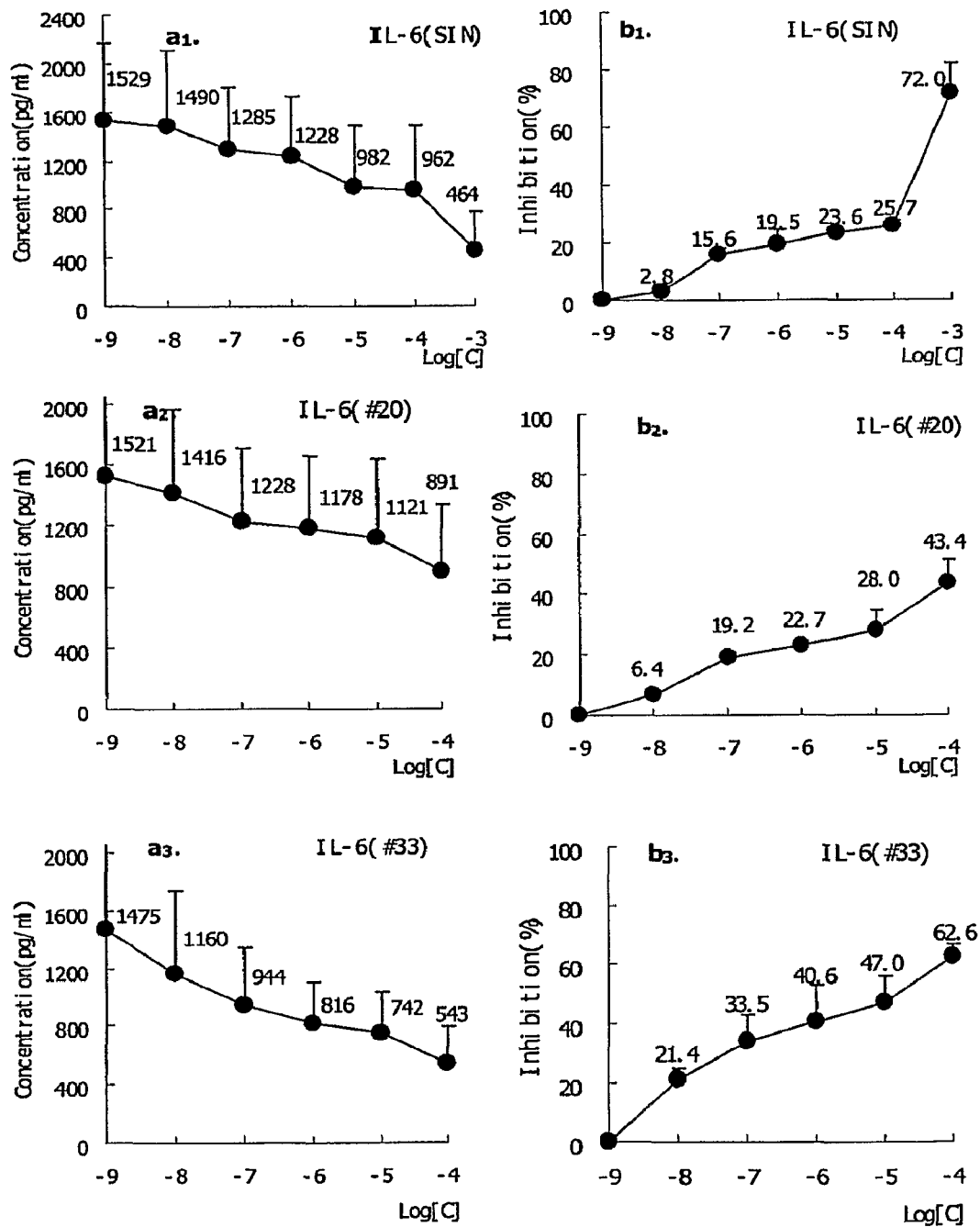
FIG. 5. The $IC_{50}$ of 5 Key Compounds for LPS-induced IL-1 Production.

FIG. 5 showed that the dose response curve of 5 key compounds to inhibit LPS-induced IL-1 production in human whole blood culture (concentration: $10^{-9}$-$10^{-5}$ mol/L). The blood samples were incubated in the presence of LPS (concentration: 10 ng/ml) for 6 h. The inhibition of Sinomenine (SIN) on LPS-induced IL-1 production was also examined. Because all tested compounds including SIN had no effect at concentration of $10^{-9}$ on LPS-induced IL-1 production, the levels of LPS-induced IL-1 production at $10^{-9}$ of tested compounds in the figures were equivalent to the levels of IL-1 in blood samples with LPS alone. Data in panel a of the figures (a1-a6) present the absolute values of IL-1; data in panel b (b1-b6) present the percentage inhibition of the tested compounds on LPS-induced IL-1 production. All data were Mean±SD (n=6).

The $IC_{50}$ of the five key compounds to inhibit LPS-induced IL-1 production was determined and summarized in the table as below:

|  | $IC_{50}$ | | | | | |
| --- | --- | --- | --- | --- | --- | --- |
|  | SIN | #33 | #39 | #20 | #37 | #48 |
| Mol/L | 0.26 | $4.4 \times 10^{-6}$ | $1.3 \times 10^{-5}$ | $5.5 \times 10^{-5}$ | $4.2 \times 10^{-4}$ | $7.6 \times 10^{-4}$ |

|  | $IC_{50}$ | | | | | |
| --- | --- | --- | --- | --- | --- | --- |
|  | SIN | #37 | #33 | #20 | #39 | #48 |
| Mol/L | 1.3 | $8.8 \times 10^{-6}$ | $1.0 \times 10^{-4}$ | $7.0 \times 10^{-4}$ | $4.9 \times 10^{-3}$ | $9.5 \times 10^{-3}$ |

5. The $IC_{50}$ of Key Compounds for LPS-Induced IL-1 Production

The inhibition of tested compounds on LPS-induced IL-1 production was assessed using human IL-1βEnzyme Immunometric Assay Kit (Lot number 145020) from Cayman Chemical Company (MI, USA). The methods are briefly described according to the instructions supplied with the Kit. All reagents and solutions were supplied with the Kit:

1) Reagents and solutions were properly prepared for the experiments to determine bioactivity according to the instruction.

2) Standard solution provided with the Kit, blood sample with testing compound and blood sample with LPS alone which were prepared as above described, 50 ul for each of these solution or blood samples, was added to each well. Then, 10 μL of DTT, 5 μL of mouse serum and 100 μL of Fab' were also added into each well together. The well was covered with the adhesive strip. Then those wells were incubated overnight at 4° C. A plate layout was provided to record standards and samples assayed.

6. The $IC_{50}$ of 5 Key Compounds for LPS-Induced IL-6 Production

The inhibition of tested compounds on LPS-induced IL-6 production was assessed using human IL-6 Elisa Kit (Lot number 054204D) from Biosource (Carlsbad, Calif., USA). The methods are briefly described according to the instruction in the Kit as below, all reagents and solutions were supplied with the Kit:

1) Reagents and solutions were properly prepared for the experiments to determine bioactivity according to the instruction of the Kit.

2) 50 μL of standard solution supplied with the Kit, blood sample with testing compound and blood sample with LPS alone was added per well. Then, 50 μL of Biotin Conjugate was added to each well. The well was covered with the adhesive strip. Then those wells were incubated for 2 hours at room temperature.

3) Each well was aspirated and washed by filling wash buffer (600 μL) using an autowasher. The liquid was completely removed at each step to ensure good performance. This process was repeated three times for a total of four washes.
4) 100 μL of Streptavidin-HRP working solution was added to each well and the well was covered with a new adhesive strip, incubated for 30 min at room temperature.
5) The same aspiration and wash procedures were repeated as described in step 3.
6) 100 μL of Stabilized Chromogen was added to each well and incubated for 30 minutes at room temperature. These wells were protected from light.
7) 100 μL of Stop Solution was added to each well.
8) The optical density of each well was determined within 30 minutes using a microplate reader set to 450 nm.

Figure 6:
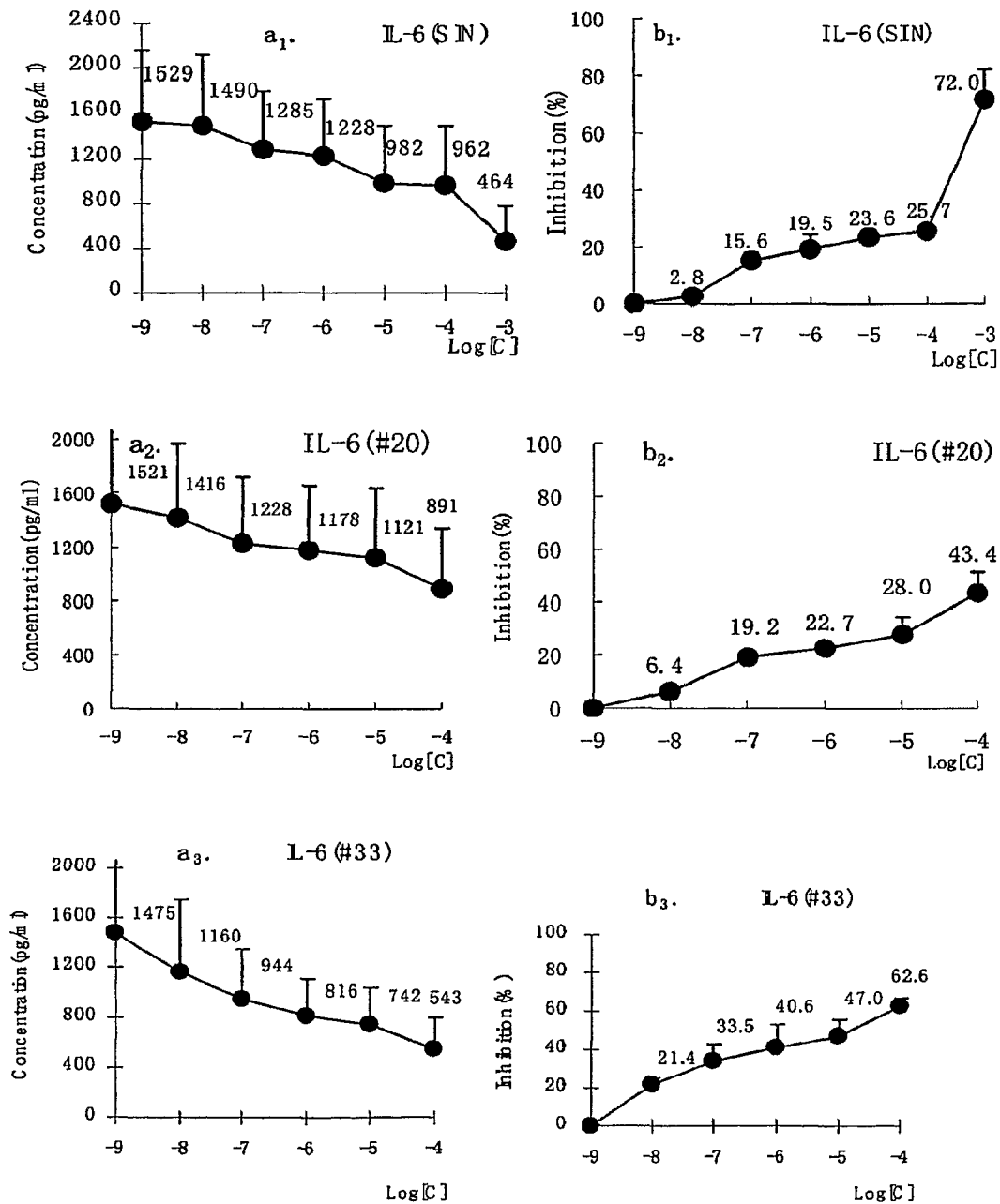
FIG. 6. The $IC_{50}$ of 5 Key Compounds for LPS-induced IL-6 Production.

FIG. 6 demonstrates that the dose response curve of 5 key compounds to inhibit LPS-induced IL-6 production in human whole blood culture (concentration: $10^{-9}$-$10^{-5}$ mol/L). The blood samples were incubated in the presence of LPS (concentration: 10 ng/ml) for 6 h. The effects of sinomenine (SIN) on LPS-induced IL-6 production were also examined. Because all tested compounds including SIN had no effect at concentration of $10^{-9}$ on LPS-induced IL-6 production, the levels of LPS-induced IL-6 production at $10^{-9}$ of tested compounds in the figures were equivalent to the levels of IL-6 in blood samples with LPS alone. Data in panel a of the figures (a1-a6) present the absolute values of IL-6; data in panel b (b1-b6) present the percentage inhibition of the tested compounds on LPS-induced IL-6 production. All data were Mean±SD (n=6).

The $IC_{50}$ of the five key compounds to inhibit LPS-induced IL-6 production was determined and summarized in the table as below:

|  | $IC_{50}$ | | | | | |
| --- | --- | --- | --- | --- | --- | --- |
|  | SIN | #39 | #33 | #20 | #48 | #37 |
| Mol/L | $1.7 \times 10^{-3}$ | $5.3 \times 10^{-6}$ | $8.7 \times 10^{-6}$ | $2.9 \times 10^{-4}$ | $1.0 \times 10^{-3}$ | 0.4 |

7. The $IC_{50}$ of 5 Key Compounds for LPS-Induced IL-8 Production

The inhibition of tested compounds on LPS-induced IL-8 production was assessed using human IL-8 Elisa Kit (Lot number 061302B) from Biosource (Carlsbad, Calif., USA). The methods are briefly described according to the instruction in the Kit as below, all reagents and solutions were supplied with the Kit:
1) Reagents and solutions were properly prepared for the experiments to determine bioactivity according to the instruction of the Kit.
2) Standard solution supplied with the Kit, blood sample with testing compound and blood sample with LPS alone was (50 μL of each item) added into per well. Then, 50 μL of Biotin Conjugate was also added to each well. The well was covered with the adhesive strip. Then those wells were incubated for 1.5 hours at room temperature.
3) Each well was aspirated and washed by filling wash buffer (600 μL) using an autowasher. The liquid was completely removed at each step to ensure good performance. This process was repeated three times for a total of four washes.
4) 100 μL of Streptavidin-HRP working solution was added to each well and the well was covered with a new adhesive strip, incubated for 30 min at room temperature.
5) The same aspiration and wash procedures were repeated as described in step 3.
6) 100 μL of Stabilized Chromogen was added to each well and incubated for 30 minutes at room temperature. These wells were protected from light.
7) 100 μL of Stop Solution was added to each well.
8) The optical density of each well was determined within 30 minutes using a microplate reader set to 450 nm.

Figure 7:
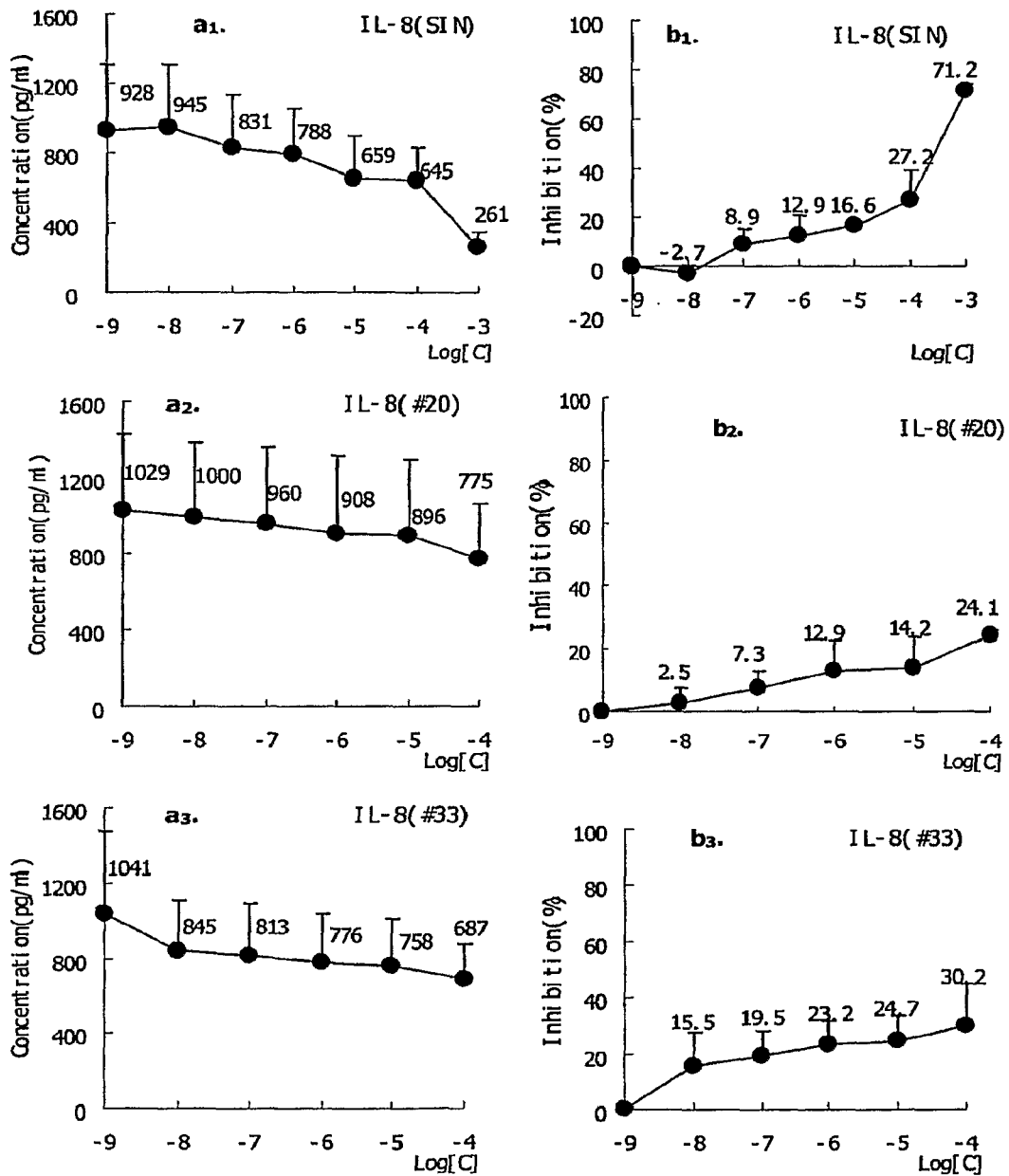
FIG. 7. The $IC_{50}$ of 5 Key Compounds for LPS-induced IL-8 Production.

FIG. 7 demonstrates that the dose response curve of 5 key compounds to inhibit LPS-induced IL-8 production in human whole blood culture (concentration: $10^{-9}$-$10^{-5}$ mol/L). The blood samples were incubated in the presence of LPS (concentration: 10 ng/ml) for 6 hours. The effects of sinomenine (SIN) on LPS-induced IL-8 production were also examined. Because all tested compounds including SIN had no effect at concentration of $10^{-9}$ on LPS-induced IL-8 production, the levels of LPS-induced IL-8 production at $10^{-9}$ of tested compounds in the figures were equivalent to the levels of IL-8 in blood samples with LPS alone. Data in panel a of the figures (a1-a6) present the absolute values of IL-8; data in panel b (b1-b6) present the percentage inhibition of the tested compounds on LPS-induced IL-8 production. All data were Mean±SD (n=6).

The $IC_{50}$ of the five key compounds to inhibit LPS-induced IL-8 production was determined and summarized in the table as below:

|  | $IC_{50}$ | | | | | |
| --- | --- | --- | --- | --- | --- | --- |
|  | SIN | #48 | #20 | #33 | #37 | #39 |
| Mol/L | $7.4 \times 10^{-5}$ | $3.8 \times 10^{-3}$ | $6.8 \times 10^{-3}$ | $7.3 \times 10^{-3}$ | $7.6 \times 10^{-3}$ | — |

What is claimed is:

1. A method for inhibiting the release of one or more cytokines in whole blood, comprising the steps of providing a whole blood culture from a subject or patient, and contacting the whole blood culture with a compound of Formula I in an amount effective to inhibit the release of one or more cytokines in the whole blood culture,

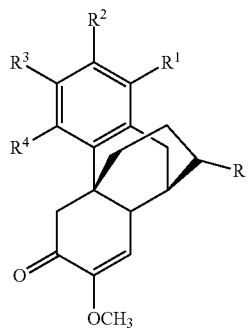

Formula I wherein
R[1] and R[2] are independently H or Br; R[3] is OMe, benzyloxy or trifluoromethoxy, R[4] is OH, and
R is cyclopentyl, cyclohexyl, cycloheptyl, allyl, cyclopropylmethyl, 2-furylmethyl, benzoylmethyl, acetylmethyl, ethoxycarbonylmethyl, 2,2,2-trifluoroethyl, benzyl, α-ethoxycarbonylbenzyl, acetyl, propanoyl, butanoyl, benzyloxycarbonyl, 3,4-methylenedioxybenzylaminocarbonyl, 2-methylphenoxy-acetyl, phenylacetyl, cyclopropylacyl, 2-furylacyl, ethylaminoacyl, nicotinoyl, benzoyl, 3-chlorobenzoyl, 4-methylbenzoyl, 2-hydroxybenzoyl, 2-chloro-4-methanesulfonylbenzoyl, 3,5-dimethylbenzoyl, 3-hydroxy-2-methylbenzoyl, 3,4-difluorobenzoyl, 2-phenylpropanoyl, methanesulfonyl, ethanesulfonyl, propanesulfonyl, p-toluenesulfonyl, aminosulfonyl, 2-methoxycarbonyl-6-methylbenzene-sulfonyl, 4-acetylamino-benzenesulfonyl, 5-chloro-1,3-dimethyl-4-pyrazolyl-methyl, 2-(6-methoxy-2-naphthyl)-propanoyl, diethylaminoglyoxylyl, 3-(piperidin-1-yl)propanoyl, phenylaminosulfonyl, benzoylaminosulfonyl, 2-(piperazin-1-yl) ethane-sulfonyl, dimethylaminomethanesulfonyl or 2-pyrimidinyl.

2. The method of claim 1, wherein R[1] and R[2] are each H; R[3] is OMe, and R[4] is OH.

3. The method of claim 1, wherein the compound is 17-(4'-methylbenzoyl)-sinomenine, 17-(2-methyl-6-methoxycarbonyl)benzenesulfonylsinomenine or 17-(5-chloro-1,3-dimethyl-4-pyrazolylmethyl sinomenine, and wherein the one or more cytokines are selected from the group consisting of TNF-α, IL-1, IL-6 and IL-8.

4. The method of claim 1, wherein the compound is 17-(pyridine-3-carbonyl)sinomenine or 17-(2-methyl-6-methoxycarbonyl)benzenesulfonyl sinomenine.

5. The method of claim 1, further comprising the steps of separating the contacted whole blood culture into cellular and non-cellular components, and measuring the level of the one or more cytokines in the non-cellular component; wherein the extent of inhibition of cytokine release by the compound is directly indicative of the responsiveness of said subject or patient to the treatment by sinomenine derivatives.

6. A method of treating arthritis in a subject, comprising administering to the subject a composition comprising a compound of Formula I and a pharmaceutically acceptable excipient or carrier, in an amount effective in treating arthritis,

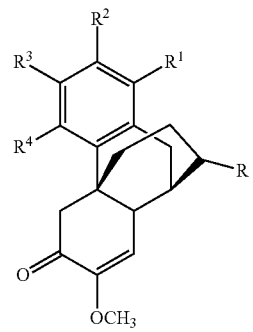

Formula I wherein
R[1] and R[2] are independently H or Br; R[3] is OMe, benzyloxy or trifluoromethoxy, R[4] is OH, and
R is cyclopentyl, cyclohexyl, cycloheptyl, allyl, cyclopropylmethyl, 2-furylmethyl, benzoylmethyl, acetylmethyl, ethoxycarbonylmethyl, 2,2,2-trifluoroethyl, benzyl, α-ethoxycarbonylbenzyl, acetyl, propanoyl, butanoyl, benzyloxycarbonyl, 3,4-methylenedioxybenzylaminocarbonyl, 2-methylphenoxy-acetyl, phenylacetyl, cyclopropylacyl, 2-furylacyl, ethylaminoacyl, nicotinoyl, benzoyl, 3-chlorobenzoyl, 4-methylbenzoyl, 2-hydroxybenzoyl, 2-chloro-4-methanesulfonylbenzoyl, 3,5-dimethylbenzoyl, 3-hydroxy-2-methylbenzoyl, 3,4-difluorobenzoyl, 2-phenylpropanoyl, methanesulfonyl, ethanesulfonyl, propanesulfonyl, p-toluenesulfonyl, aminosulfonyl, 2-methoxycarbonyl-6-methylbenzene-sulfonyl, 4-acetylamino-benzenesulfonyl, 5-chloro-1,3-dimethyl-4-pyrazolyl-methyl, 2-(6-methoxy-2-naphthyl)-propanoyl, diethylaminoglyoxylyl, 3-(piperidin-1-yl)propanoyl, phenylaminosulfonyl, benzoylaminosulfonyl, 2-(piperazin-1-yl) ethane-sulfonyl, dimethylaminomethanesulfonyl or 2-pyrimidinyl.

7. The method of claim 6, wherein R[1] and R[2] are each H; R[3] is OMe, and R[4] is OH.

8. The method of claim 6, wherein the arthritis is rheumatoid arthritis or osteoarthritis.

* * * * *